(12) United States Patent
Myers et al.

(10) Patent No.: US 6,376,472 B1
(45) Date of Patent: Apr. 23, 2002

(54) COMPOUNDS HAVING ANTIHYPERTENSIVE, CARDIOPROTECTIVE, ANTI-ISCHEMIC AND ANTILIPOLYTIC PROPERTIES

(75) Inventors: Michael R. Myers, Reading, PA (US); Martin P. Maguire, Woburn, MA (US); Alfred P. Spada, Lansdale, PA (US); William R. Ewing, Downingtown, PA (US); Henry W. Pauls; Yong Mi Choi-Sledeski, both of Collegeville, PA (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 09/174,191

(22) Filed: Oct. 16, 1998

Related U.S. Application Data

(63) Continuation-in-part of application No. PCT/US97/11320, filed on Jul. 1, 1997
(60) Provisional application No. 60/021,366, filed on Jul. 8, 1996.
(51) Int. Cl.$^7$ ............... C07D 473/34; C07D 471/04; A61K 31/52; A61K 31/437; A61P 9/10
(52) U.S. Cl. ............... 514/44; 536/27.14; 536/27.3; 536/27.62; 544/277
(58) Field of Search ............... 544/277; 536/27.14, 536/27.3, 27.62; 514/46, 266

(56) References Cited

U.S. PATENT DOCUMENTS

| | | |
|---|---|---|
| 4,954,504 A | 9/1990 | Chen et al. |
| 5,043,325 A | 8/1991 | Olsson et al. |
| 5,364,862 A | 11/1994 | Spada et al. |
| 5,561,134 A | 10/1996 | Spada et al. |
| 5,736,554 A | 4/1998 | Spada et al. |

Primary Examiner—Mark L. Berch
(74) Attorney, Agent, or Firm—Paul R. Darkes; Peter Butch; Irving Newman

(57) ABSTRACT

A compound of the formula

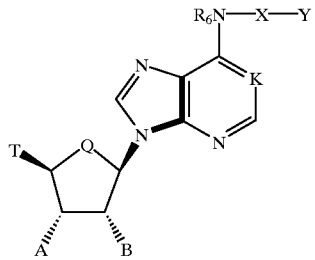

wherein K is N; Q is $CH_2$ or O; $R_6$ is hydrogen, alkyl, allyl, 2-methylallyl, 2-butenyl, or cycloalkyl X is 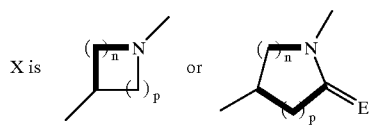

where the nitrogen of the ring of X is substituted by Y; E is O or S; Y is hydrogen, alkyl, aralkyl, substituted aralkyl, aryl, substituted aryl, heterocyclyl, substituted heterocyclyl, heterocyclylalkyl, or substituted heterocyclylalkyl; and n and p are independently 0, 1, 2, or 3, provided that n+p is at least 1;

T is hydrogen, alkyl, alkylcarbonyl, alkylthiocarbonyl, halo, carboxyl,

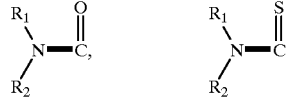

A and B are independently hydrogen, alkyl, hydroxyalkyl, alkoxyalkyl, or OR';

or a pharmaceutically acceptable salt thereof, a pharmaceutic-ally acceptable prodrug thereof, an N-oxide thereof, a hydrate thereof or a solvate thereof.

15 Claims, No Drawings

COMPOUNDS HAVING ANTIHYPERTENSIVE, CARDIOPROTECTIVE, ANTI-ISCHEMIC AND ANTILIPOLYTIC PROPERTIES

CROSS REFERENCE TO RELATED APPLICATIONS

This is a continuation-in-part of International Patent Application Number PCT/US97/11320, filed Jul. 1, 1997, which claims the benefit of U.S. Ser. No. 60/021,366, filed Jul. 8, 1996, now abandoned.

BACKGROUND OF THE INVENTION

1. Field of the Invention

This invention relates to compounds derived from adenosine and analogues thereof, to pharmaceutical compositions containing such compounds, to their use in treating hypertension and myocardial ischemia, to their use as cardioprotective agents which ameliorate ischemic injury or myocardial infarct size consequent to myocardial ischemia, and to their use as antilipolytic agents which reduce plasma lipid levels, serum triglyceride levels, and plasma cholesterol levels, and to methods and intermediates used in the preparation of such compounds.

Hypertension

Hypertension, a condition of elevated blood pressure, affects a substantial number of the human population. Consequences of persistent hypertension include vascular damage to the ocular, renal, cardiac and cerebral systems, and the risk of these complications increases as blood pressure increases. Basic factors controlling blood pressure are cardiac output and peripheral vascular resistance, with the latter being the predominant common mechanism which is controlled by various influences. The sympathetic nervous system regulates peripheral vascular resistance through direct effects on alpha- and beta-adrenergic receptors as well as through indirect effects on renin release. Drug therapy is aimed at specific components of these blood pressure regulatory systems, with different mechanisms of action defining the several drug classes including diuretics, beta-adrenergic receptor antagonists (beta-blockers), angiotensin-converting enzyme (ACE) inhibitors, and calcium channel antagonists.

Thiazide-type diuretics are used in hypertension to reduce peripheral vascular resistance through their effects on sodium and water excretion. This class of drugs includes hydrochlorothiazide, chlorothiazide, methyclothiazide, and cyclothiazide, as well as related agents indapamide, metolazone, and chlorthalidone. Although the beta-blocker mechanism of action was once believed to be blockade of the $beta_1$-adrenergic receptor subtype in the heart to reduce heart rate and cardiac output, more recent beta-blockers with intrinsic sympathomimetic activity (ISA), including pindolol, acebutolol, penbutolol, and carteolol, are as effective as non-ISA beta-blockers, causing less reduction in heart rate and cardiac output. Other postulated mechanisms for these drugs include inhibition of renin release, a central effect, and an effect at pre-synaptic beta-adrenergic receptors resulting in inhibition of norepinephrine release. Cardioselective beta-blockers metoprolol (Lopressor-Geigy), acebutolol (Sectral-Wyeth), and atenolol (Tenormin-1CI), at low doses, have a greater effect on $beta_1$-adrenergic receptors than on $beta_2$-adrenergic receptor subtypes located in the bronchi and blood vessels. Nonselective beta-blockers act on both beta-adrenergic receptor subtypes and include propranolol (Inderal-Ayerst), timolol (Blocadren-Merck), nadolol (Corgard-Squibb), pindolol (Visken-Sandoz), penbutolol (Levatol-Hoechst-Roussel), and carteolol (Cartrol-Abbott). Adverse effects of beta-blockers include asymptomatic bradycardia, exacerbation of congestive heart failure, gastrointestinal disturbances, increased airway resistance, masked symptoms of hypoglycemia, and depression. They may cause elevation of serum triglycerides and may lower high-density lipoprotein cholesterol.

ACE inhibitors prevent the formation of angiotensin II and inhibit breakdown of bradykinin. Angiotensin II is a potent vasoconstrictor and also stimulates the secretion of aldosterone. By producing blockade of the renin-angiotensin-aldosterone system, these agents decrease peripheral vascular resistance, as well as sodium and water retention. In addition, ACE inhibitors increase levels of bradykinin and prostaglandins, endogenous vasodilators. Captopril (Capoten-Squibb) and Enalapril (Vasotec-Merck) are the leading ACE inhibitors. Adverse effects of the ACE inhibitors include rash, taste disturbance, proteinuria, and neutropenia.

The calcium channel antagonists reduce the influx of calcium into vascular smooth muscle cells and produce systemic vasodilation, resulting in their antihypertensive effect. Other effects of calcium channel antagonists include interference with action of angiotensin II and $alpha_2$-adrenergic receptor blockade, which may add to their antihypertensive effects. Calcium channel antagonists do not have the adverse metabolic and pharmacologic effects of thiazides or beta-blockers and may therefore be useful in patients with diabetes, peripheral vascular disease, or chronic obstructive pulmonary disease. Two calcium channel antagonists, Verapamil and diltiazem, have serious adverse cardiovascular effects on atrioventricular cardiac conduction in patients with preexisting conduction abnormalities, and they may worsen bradycardia, heart block, and congestive heart failure. Other minor adverse effects of calcium channel antagonists include peripheral edema, dizziness, light-headedness, headache, nausea, and flushing, especially with nifedipine and nicardipine.

Many other agents are available to treat essential hypertension. These agents include prazosin and terazocin, $alpha_1$-adrenergic receptor antagonists whose antihypertensive effects are due to resultant arterial vasodilation; clonidine, an $alpha_2$-adrenergic agonist which acts centrally as well as peripherally at inhibitory $alpha_2$-adrenergic receptors, decreasing sympathetic response. Other centrally acting agents include methyldopa, guanabenz, and guanfacine; reserpine, which acts by depleting stores of catecholamines; guanadrel, a peripheral adrenergic antagonist similar to guanethidine with a shorter duration of action; and direct-acting vasodilators such as hydralazine and minoxidil. These agents, although effective, produce noticeable symptomatic side effects, including reflex sympathetic stimulation and fluid retention, orthostatic hypotension, and impotence.

Many antihypertensive agents activate compensatory pressor mechanisms, such as increased renin release, elevated aldosterone secretion and increased sympathetic vasoconstrictor tone, which are designed to return arterial pressure to pretreatment levels, and which can lead to salt and water retention, edema and ultimately to tolerance to the antihypertensive actions of the agent. Furthermore, due to the wide variety of side effects experienced with the present complement of antihypertensive drugs and the problems experienced therewith by special populations of hypertensive patients, including the elderly, blacks, and patients with chronic obstructive pulmonary disease, diabetes, or peripheral vascular diseases, there is a need for additional classes of drugs to treat hypertension.

Ischemia

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone. Mechanisms for vasospastic ischemia include: (i) Increased vascular tone at the site of stenosis due to increased catecholamine release: (ii) Transient intraluminal plugging and (iii) Release of vasoactive substances formed by platelets at the site of endothelial lesions.

The coronary circulation is unique since it perfuses the organ which generates the perfusion pressure for the entire circulation. Thus, interventions which alter the state of the peripheral circulation and contractility will have a profound effect on coronary circulation. The regulatory component of the coronary vasculature is the small coronary arterioles which can greatly alter their internal diameter. The alteration of the internal radius is the result of either intrinsic contraction of vascular smooth muscle (autoregulation) or extravascular compression due to ventricular contraction. The net effect of therapies on the ischemic problem involves a complex interaction of opposing factors which determine the oxygen supply and demand.

Cardioprotection and Prevention of Ischemic Injury

The development of new therapeutic agents capable of limiting the extent of myocardial injury, i.e., the extent of myocardial infarction, following acute myocardial ischemia is a major concern of modern cardiology.

The advent of thrombolytic (clot dissolving) therapy during the last decade demonstrates that early intervention during heart attack can result in significant reduction of damage to myocardial tissue. Large clinical trials have since documented that thrombolytic therapy decreases the risk of developing disturbances in the heartbeat and also maintains the ability of the heart to function as a pump. This preservation of normal heart function has been shown to reduce long-term mortality following infarction.

There has also been interest in the development of therapies capable of providing additional myocardial protection which could be administered in conjunction with thrombolytic therapy, or alone, since retrospective epidemiological studies have shown that mortality during the first few years following infarction appears to be related to original infarct size.

In preclinical studies of infarction, conducted in a variety of animal models, many types of pharmacological agents such as calcium channel blockers, prostacyclin analogues, and agents capable of inhibiting certain metabolic pathways have been shown to be capable of reducing ischemic injury in several animal species.

Recent studies have demonstrated that exposure of the myocardium to brief periods of ischemia (interruption of blood flow to the heart) followed by reperfusion (restoration of blood flow) is able to protect the heart from the subsequent ischemic injury that would otherwise result from subsequent exposure to a longer period of ischemia. This phenomenon has been termed myocardial preconditioning and is believed to be partially attributable to the release of adenosine during the preconditioning period.

Other studies have shown that adenosine and adenosine analogues reduce the extent of tissue damage that is observed following the interruption of blood flow to the heart in a variety of models of ischemic injury in several species (see, for example, Toombs, C. et al., "Myocardial protective effects of adenosine. Infarct size reduction with pretreatment and continued receptor stimulation during ischemia.", *Circulation* 86, 986–994 (1992); Thornton, J. et al., "Intravenous pretreatment with $A_1$-selective adenosine analogues protects the heart against infarction.", *Circulation* 85, 659–665 (1992); and Downey, J., "Ischemic preconditioning—nature's own cardioprotective intervention.", *Trends Cardiovasc. Med.* 2(5), 170–176 (1992)).

Compounds of the present invention mimic myocardial preconditioning, thereby ameliorating ischemic injury or producing a reduction in the size of myocardial infarct consequent to myocardial ischemia and are thereby useful as cardioprotective agents.

Antilipolysis

Hyperlipidemia and hypercholesterolemia are known to be two of the prime risk factors for atherosclerosis and coronary heart disease, the leading cause of death and disability in Western countries. Although the etiology of atherosclerosis is multifactorial, the development of atherosclerosis and conditions including coronary artery disease, peripheral vascular idsease and cerbrovascular disease resulting from restricted blood flow, are associated with abnormalities in serum cholesterol and lipid levels. The etiology of hypercholesterolemia and hyperlipidemia is primarily genetic, although factors such as dietary intake of saturated fats and cholesterol may contribute.

The antilipolytic activity of adenosine and adenosine analogues arises from the activation of the $A_1$ receptor subtype (Lohse, M. J., et al., *Recent Advances in Receptor Chemistry*, Melchiorre, C. and Gianella, Eds, Elsevier Science Publishers B.V., Amsterdam, 1988, 107–121). Stimulation of this receptor subtype lowers the intracellular cyclic AMP concentration in adipocytes. Cyclic AMP is a necessary co-factor for the enzyme lipoprotein lipase which hydrolytically cleaves triglycerides to free fatty acids and glycerol in adipocytes (Egan, J. J., et al., *Proc. Natl. Acad. Sci.* 1992 (89), 8357–8541). Accordingly, reduction of intracellular cyclic AMP concentration in adipocytes reduces lipoprotein lipase activity and, therefore, the hydrolysis of triglycerides.

Elevated blood pressure and plasma lipids, including triglycerides, are two well accepted risk factors associated with mortality resulting from cardiovascular disease.

For the diabetic patient, where the likelihood of mortality from cardiovascular disease is substantially greater, the risk associated with these factors is further magnified (Bierman, E. L., *Arteriosclerosis and Thrombois* 1992 (12), 647–656). Additionally, data suggest that excessive lipolysis is characteristic of non-insulin dependent diabetes and possibly contributes to insulin resistance and hyperglycemia (Swislocki, A. L., *Horm. Metab. Res.* 1993 (25), 90–95).

Compounds of the present invention, as antihypertensive and antilipolytic agents, are useful in the treatment and amelioration of both vascular and metabolic risk factors, and are of particular value and utility.

The present invention relates to a class of adenosine analogues and their utility in the treatment of hypertension, myocardial ischemia, as cardioprotective agents which ameliorate ischemic injury or myocardial infarct size consequent to myocardial ischemia, and as antilipolytic agents which reduce plasma lipid levels, serum triglyceride levels, and plasma cholesterol levels, and to methods and intermediates used in the preparation of such compounds.

2. Reported Developments

Adenosine has a wide variety of physiological and pharmacological actions including a marked alteration of cardiovascular and renal function. In animals and man, intravenous injection of the adenosine nucleotide causes hypotension.

The physiological and pharmacological actions of adenosine are mediated through specific receptors located on cell surfaces. Four adenosine receptor subtypes, designated as A1, $A_{2A}$, $A_{2B}$, and $A_3$ receptors, have been identified. The $A_1$ receptor inhibits the formation of cAMP by suppressing the activity of adenylate cyclase, while stimulation of $A_2$ receptors increases adenylate cyclase activity and intracellular cAMP. Each receptor appears to mediate specific actions of adenosine in different tissues: for example, the vascular actions of adenosine appears to be mediated through stimulation of $A_2$ receptors, which is supported by the positive correlation between cAMP generation and vasorelaxation in adenosine-treated isolated vascular smooth muscle; while stimulation of the cardiac $A_1$ receptors reduces cAMP generation in the heart which contributes to negative dromotropic, inotropic and chronotropic cardiac effects. Consequently, unlike most vasodilators, adenosine administration does not produce a reflex tachycardia.

Adenosine also exerts a marked influence on renal function. Intrarenal infusion of adenosine causes a transient fall in renal blood flow and an increase in renal vascular resistance. With continued infusion of adenosine, renal blood flow returns to control levels and renal vascular resistance is reduced. The initial renal vasoconstrictor responses to adenosine are not due to direct vasoconstrictor actions of the nucleotide, but involve an interaction between adenosine and the renin-angiotensin system.

Adenosine is widely regarded as the primary physiological mediator of reactive hyperemia and autoregulation of the coronary bed in response to myocardial ischemia. It has been reported that the coronary endothelium possesses adenosine $A_2$ receptors linked to adenylate cyclase, which are activated in parallel with increases in coronary flow and that cardiomyocyte receptors are predominantly of the adenosine $A_1$ subtype and associated with bradycardia. Accordingly, adenosine offers a unique mechanism of ischemic therapy.

Cardiovascular responses to adenosine are short-lived due to the rapid uptake and metabolism of the endogenous nucleotide. In contrast, the adenosine analogues are more resistant to metabolic degradation and are reported to elicit sustained alterations in arterial pressure and heart rate.

Several potent metabolically-stable analogues of adenosine have been synthesized which demonstrate varying degrees of selectivity for the two receptor subtypes. Adenosine agonists have generally shown greater selectivity for $A_1$ receptors as compared to $A_2$ receptors. Cyclopentyladenosine (CPA) and R-phenylisopropyl-adenosine (R-PIA) are standard adenosine agonists which show marked selectivity for the $A_1$ receptor ($A_2/A_1$ ratio=780 and 106, respectively). In contrast, N-5'-ethyl-carboxamido adenosine (NECA) is a potent $A_2$ receptor agonist (Ki--12 nM) but has equal affinity for the $A_1$ receptor (Ki–6.3 nM; $A_2/A_1$ ratio=1.87).

Until recently, CV-1808 was the most selective $A_2$ agonist available ($A_2/A_1$=0.19), even though the compound was 10-fold less potent than NECA in its affinity for the $A_2$ receptor. In recent developments, newer compounds have been disclosed which are very potent and selective $A_2$ agonists (Ki=3–8 nM for $A_1$; $A_2/A_1$ ratio=0.027–0.042) (C. E. Müller and T. Scior, *Pharmaceutica Aca Hevetiae* 68 (1993) 77–111).

Various N6-aryl and N6-heteroarylalkyl substituted adenosines, and substituted-(2-amino and 2-hydroxy) adenosines, have been reported in the literature as possessing varied pharmacological activity, including cardiac and circulatory activity. See, for example, British Patent Specification 1,123,245, German Offen. 2,136,624, German Off 2,059,922, German Offen. 2,514,284, South African Patent No. 67/7630, U.S. Pat. No. 4,501,735, EP Publication No. 0139358 (disclosing N6-[geminal diaryl substiuted alkyl] adenosines), EP Patent Application Ser. No. 88106818.3 (disclosing that N6-heterocyclic-substituted adenosine derivatives exhibit cardiac vasodilatory activity), German Offen. 2,131,938 (disclosing aryl and heteroaryl alkyl hydrazinyl adenosine derivatives), German Offen. 2,151,013 (disclosing N6-aryl and heteroaryl substituted adenosines), German Offen. 2,205,002 (disclosing adenosines with N6-substituents comprising bridged ring structures linking the N6-nitrogen to substituents including thienyl) and South African Patent No. 68/5477 (disclosing N6-indolyl substituted-2-hydroxy adenosines).

U.S. Pat. No. 4,954,504 and EP Publication No. 0267878 disclose generically that carbocyclic ribose analogueues of adenosine, and pharmaceutically acceptable esters thereof, substituted in the 2- and/or N6- positions by aryl lower alkyl groups including thienyl, tetrahydropyranyl, tetrahydrothiopyranyl, and bicyclic benzo fused 5- or 6- membered saturated heterocyclic lower alkyl derivatives exhibit adenosine receptor agonist properties. Adenosine analogueues having thienyl-type substituents are described in EP Publication No. 0277917 (disclosing N6-substituted-2-heteroarylalkylamino substituted adenosines including 2-[(2-[thien-2-yl]ethyl)amino]substituted adenosine), German Offen. 2,139,107 (disclosing N6-[benzothienylmethyl]-adenosine), PCT WO 85/04882 (disclosing that N6-heterocyclicalkyl-substituted adenosine derivatives, including N6-[2-(2-thienyl)ethyl]amino-9-(D-ribofuranosyl)9H-purine, exhibit cardiovascular vasodilatory activity and that N6-chiral substituents exhibit enhanced activity), EP Published Application No. 0232813 (disclosing that N6-(1-substituted thienyl) cyclopropylmethyl substituted adenosines exhibit cardiovascular activity), U.S. Pat. No. 4,683,223 (disclosing that N6-benzothiopyranyl substituted adenosines exhibit antihypertensive properties), PCT WO 88/03147 and WO 88/03148 (disclosing that N6-[2-aryl-2-(thien-2-yl)]ethyl substituted adensosines exhibit antihypertensive properties), U.S. Pat. Nos. 4,636,493 and 4,600,707 (disclosing that N6-benzothienylethyl substituted adenosines exhibit antihypertensive properties).

Adenosine-5'-carboxylic acid amides are disclosed as having utility as anti-hypertensive and anti-anginal agents in U.S. Pat. No. 3,914,415, while U.S. Pat. No. 4,738,954 discloses that N6-substituted aryl and arylalkyl-adenosine 5'-ethyl carboxamides exhibit various cardiac and antihypertensive properties.

$N^6$-alkyl-2'-O-alkyl adenosines are disclosed in EP Publication No. 0,378,518 and UK Patent Application No. 2,226,027 as having antihypertensive activity. $N^6$-alkyl-2', 3'-di-O-alkyl adenosines are also reported to have utility as antihypertensive agents, U.S. Pat. No. 4,843,066.

Adenosine-5'-(N-substituted)carboxamides and carboxylate esters and N1-oxides thereof are reported to be coronary vasodilators, Stein, et al., *J. Med. Chem.* 1980, 23, 313–319 and *J. Med. Chem.* 19 (10), 1180 (1976). Adenosine-5'-carboxamides and N1-oxides thereof are also reported as small animal poisons in U.S. Pat. No. 4,167,565.

The antilipolytic activity of adenosine is described by Dole, V. P., *J. Biol. Chem.* 236 (12), 3125–3130 (1961). Inhibition of lipolysis by (R)- $N^6$ phenylisopropyl adenosine is disclosed by Westermann, E., et al., *Adipose Tissue, Regulation and Metabolic Functions*, Jeanrenaud, B. and Hepp, D. Eds., George Thieme, Stuttgart, 47–54 (1970). $N^6$-mono- and disubstituted adenosine analogueues are disclosed as having antilipolytic, antihypercholesterolemic, and antihyperlipemic activity in U.S. Pat. Nos. 3,787,391; 3,817,981; 3,838,147; 3,840,521; 3,835,035; 3,851,056; 3,880,829; 3,929,763; 3,929,764; 3,988,317; and 5,032,583.

N6-substituted adenosines and analogues, useful in treating gastroinstestinal motility disorders, have been reported in EP Published Applications Nos. 0423776, and 0423777.

N6-heterocyclyl compounds derived from adenosine and analogues thereof, and their use in treating hypertension and myocardial ischemia, their use as cardioprotective agents which ameliorate ischemic injury or myocardial infarct size consequent to myocardial ischemia, their use as antilipolytic agents which reduce plasma lipid levels, serum triglyceride levels, and plasma cholesterol levels, are disclosed in U.S. patent application Ser. No. 08/316,761, filed Oct. 3, 1994, assigned to the same assignee as the present application, and for which a Notice of Allowance was mailed Mar. 26, 1996. N6-heterocyclyl compounds derived from adenosine and analogues thereof, and their use in treating myocardial ischemia and hypertension, are also disclosed in U.S. Pat. No. 5,364,862, filed Oct. 2, 1992, and which is assigned to the same assignee as the present application.

It is believed that the reported toxicity, CNS properties and heart rate elevation associated with adenosine analogueues have contributed to the difficulties preventing the development of a commercial adenosine analogue antihypertensive/antiischemic agent. The present invention relates to a class of metabolically stable adenosine analogues, and derivatives thereof, possessing unexpectedly desirable pharmacological properties, i.e. are anti-hypertensive, cardioprotective, anti-ischemic, and antilipolytic agents having a unique therapeutic profile.

SUMMARY OF THE INVENTION

The compounds of the present invention are described by Formula I

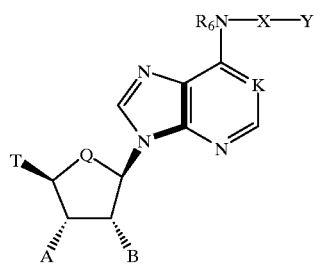

Formula I wherein:
K is N, NO, or CH;
Q is $CH_2$ or O;

$R_6$ is hydrogen, alkyl, allyl, 2-methylallyl, 2-butenyl, or cycloalkyl;

X is 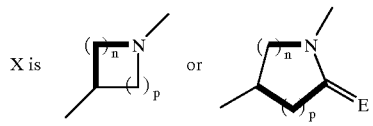

where the nitrogen of the ring of X is substituted by Y;
E is O or S;
Y is hydrogen, alkyl, aralkyl, substituted aralkyl, aryl, substituted aryl, heterocyclyl, substituted heterocyclyl, heterocyclylalkyl, or substituted heterocyclylalkyl;
n and p are independently 0, 1, 2, or 3, provided at n+p is at least 1;
T is hydrogen, alkyl, acyl, thioacyl, halo, carboxyl,

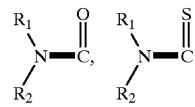

or $R_3O$—$CH_2$;
$R_1$, $R_2$, and $R_3$ are independently H, alkyl, or cycloalkyl;
A is hydrogen, alkyl, hydroxyalkyl, alkoxyalkyl, or OR';
B is hydrogen, alkyl, hydroxyalkyl, alkoxyalkyl, or OR";
R' and R" are independently hydrogen, alkyl, aralkyl, carbamoyl, alkyl carbamoyl, dialkylcarbamoyl, acyl, alkoxycarbonyl, aralkoxycarbonyl, aryloxycarbonyl, or, when A and B are OR' and OR", respectively, R' and R" together may form

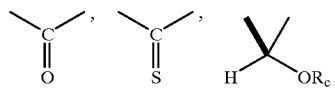

where $R_c$ is hydrogen or alkyl

where $R_d$ and $R_e$ are independently hydrogen, alkyl, or together with the carbon atom to which they are attached may form a 1,1-cycloalkyl group;
or a pharmaceutically acceptable salt thereof, pharmaceutically acceptable prodrug thereof, an N-oxide thereof, a hydrate thereof or a solvate thereof.

This invention relates also to methods for treating cardiovascular disease marked by hypertension or myocardial ischemia using pharmaceutical compositions including an anti-hypertensive effective amount or an anti-ischemic effective amount of a compound of Formula I above, to a method for ameliorating ischemic injury or myocardial infarct size using pharmaceutical compositions including a cardioprotective amount of a compound of Formula I above, to a method for treating hyperlipidemia or hypercholesterolemia using pharmaceutical compositions including an antilipolytic amount of Formula I, and to methods and intermediates used in the preparation of such compounds.

DETAILED DESCRIPTION

As used above and throughout the description of the invention, the following terms, unless otherwise indicated, shall be understood to have the following meanings:

"Acyl" means a straight or branched alkyl-C=O group. "Thioacyl" means a straight or branched alkyl-C=S group. Preferred acyl and thioacyl groups are lower alkanoyl and lower thioalkanoyl having from 1 to about 6 carbon atoms in the alkyl group.

"Alkyl" means a saturated aliphatic hydrocarbon group which may be straight or branched and having about 1 to about 20 carbon atoms in the chain. Preferred alky groups may be straight or branched and have about 1 to about 10 carbon atoms in the chain. Branched means that a lower alkyl group such as methyl, ethyl or propyl is attached to a linear alkyl chain.

"Lower alkyl" means an alkyl group having 1 to about 6 carbons.

"Cycloalkyl" means an aliphatic ring having 3 to about 10 carbon atoms in the ring. Preferred cycloalkyl groups have 4 to about 7 carbon atoms in the ring.

"Carbamoyl" means an

group. Alkylcarbamoyl and dialkylcarbamoyl means that the nitrogen of the carbamoyl is substituted by one or two alkyl groups, respectively.

"Carboxyl" means a COOH group.

"Alkoxy" means an alkyl-O group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group, as previously described, substituted by an alkoxy group, as previously described.

"Alkoxycarbonyl means an alkoxy-C=O group.

"Aralkyl" means an alkyl group substituted by an aryl radical, wherein "aryl" means a phenyl or naphthyl. "Substituted aralkyl" and "substituted aryl" means that the aryl group, or the aryl group of the aralkyl group is substituted with one or more substituents which include alkyl, alkoxy, amino, nitro, carboxy, carboalkoxy, cyano, alkyl amino, halo, hydroxy, hydroxyalkyl, mercaptyl, alkylmercaptyl, trihaloalkyl, carboxyalkyl or carbamoyl.

"Aralkoxycarbonyl" means an aralkyl—O—C=O group.

"Aryloxycarbonyl" means an aryl—O—C=O group.

"Carbalkoxy" means a carboxyl substituent esterified with an alcohol of the formula $C_nH_{2n+1}OH$, wherein n is from 1 to about 6.

"Halogen" (or "halo") means chlorine (chloro), fluorine (fluoro), bromine (bromo) or iodine (iodo).

"Heterocyclyl" means about a 4 to about a 10 membered ring structure in which one or more of the atoms in the ring is an element other than carbon, e.g., N, O or S. Heterocyclyl may be aromatic or non-aromatic, i.e., may be saturated, partially or fully unsaturated.

Preferred heterocyclyl groups include pyridyl, pyridazinyl, pyrimidinyl, isoquinolinyl, quinolinyl, quinazolinyl, imidazolyl, pyrrolyl, furanyl, thienyl, thiazolyl, benzothiazolyl, piperidinyl, pyrrolidinyl, tetrahydrofuranyl, tetrahydropyranyl, and morphonlinyl groups.

"Substituted heterocyclyl" means that the heterocyclyl group is substituted by one or more substituents wherein the substituents include alkoxy, alkylamino, aryl, carbalkoxy, carbamoyl, cyano, halo, heterocyclyl, trihalomethyl, hydroxy, mercaptyl, alkylmercaptyl or nitro.

"Hydroxyalkyl" means an alkyl group substituted by a hydroxy group. Hydroxy lower alkyl groups are preferred. Exemplary preferred groups include hydroxymethyl, 2-hydroxymethyl, 2-hydroxypropyl and 3-hydroxypropyl.

"Prodrug" means a compound which is rapidly transformed in vivo to yield the parent peptide compound, for example by hydrolysis in blood. "Pharmaceutically acceptable prodrug" means a compound which is, within the scope of sound medical judgement, suitable for pharmaceutical use in a patient without undue toxicity, irritation, allergic response, and the like, and effective for the intended use, including a pharmaceutically acceptable ester as well as a zwitterionic form, where possible, of the peptide compounds of the invention. Pharmaceutically acceptable prodrugs according to the invention are described in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Cardioprotection" refers to the effect whereby the myocardium is made less susceptible to ischemic injury and myocardial infarct consequent to myocardial ischemia.

"Amelioration of ischemic injury" means the prevention or reduction of ischemic injury to the myocardium consequent to myocardial ischemia.

"Amelioration of myocardial infarct size" means the reduction of the myocardial infarct size, or the prevention of myocardial infarct, consequent to myocardial ischemia.

The compounds of Formula I contain chiral (asymmetric) centers. The invention includes the individual stereoisomers and mixtures thereof. The individual isomers are prepared or isolated by methods well known in the art or by methods described herein.

The compounds of the invention may be used in the form of the free base, in the form of acid addition salts or as hydrates. All such forms are within the scope of the invention. Acid addition salts are simply a more convenient form for use. In practice, use of the salt form inherently amounts to use of the base form. The acids which may be used to prepare the acid addition salts include preferably those which produce, when combined with the free base, pharmaceutically acceptable salts, that is, salts whose anions are non-toxic to the recipient in pharmaceutical doses of the salts, so that the beneficial anti-hypertensive, cardioprotective, anti-ischemic, and antilipolytic effects produced by the free base are not vitiated by side effects ascribable to the anions. Although pharamaceutically acceptable salts of the compounds of the invention are preferred, all acid addition salts are useful as sources of the free base form, even if the particular salt, per se, is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid, and sulfamic acid; and organic acids such as acetic acid, citric acid, lactic acid, tartaric acid, malonic acid, methanesulfonic acid, fumaric acid, ethanesulfonic acid, benzenesulfonic acid, p-toluenesulfonic acid, cyclohexylsulfamic acid, quinic acid and the like. The corresponding acid addition salts comprise the following: hydrochloride, sulfate, phosphate, sulfamate, acetate, citrate, lactate, tartarate, methanesulfonate, fumarate, ethanesulfonate, benzenesulfonate, p-toluenesulfonate, cyclohexylsulfonate and quinate, respectively.

The acid addition salts of the compounds of the invention are conveniently prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Included within the scope of Formula I are classes of compounds which may be characterized generally as N6-substituted adenosines; N6-substituted carbocyclic adenosines (or, alternatively, dihydroxy[N6-substituted-9-adenyl] cyclopentanes) and N-oxides thereof; and N6-substituted-N'-1-deazaaristeromycins (or, alternatively, dihydroxy[N7-substituted[4,5-b]imidazopyridyl]-cyclopentanes). Also within the scope of Formula I are the 5'-alkylcarboxamide derivatives of the adenosines, the carbocyclic adenosines and the 1-deazaaristeromycins, the derivatives of compounds of the above classes in which one or both of the 2- or 3- hydroxyl groups of the cyclopentane ring or, in the cases of classes of compounds containing the ribose moiety, the 2'- or 3'- hydroxyl groups of the ribose ring are substituted. Such derivatives may themselves comprise the biologically active chemical entity useful in the treatment of hypertension and myocardial ischemia, and as cardioprotective and antilipolytic agents, or may act as pro-drugs to such biologically active compounds which are formed therefrom under physiological conditions.

Representative compounds of the invention include: (2R,3R,4S,5R)-2-hydroxymethyl-5-[6-[1-(5-chloropyridin-2-yl)-pyrrolidin-3(S)-ylamino]-purin-9-yl]-tetrahydrofuran-3,4-diol, (2R,3S,4R,5R)-2-hydroxymethyl-5-[6-[1-(5-trifluoromethylpyridin-2-yl)-pyrrolidin-3(R)-ylamino]-purin-9-yl]tetrahydrofuran-3,4-diol, (2R,3R,4S,5R)-2-hydroxymethyl-5-[6-[1-(5-trifluoromethylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(4-trifluoromethylpyridin-2-yl)-pyrrolidin-3(S)ylamino]-purin-9-yl]tetrahydrofuran-3,4-diol, (2R,3R,4S,5R) 2-hydroxymethyl-5-[6-[1-(5-bromopyridin-2-yl)-pyrrolidin-3(S)-ylamino]-purin-9-yl]-tetrahydrofuran-3,4-diol, (2R,3R,4S,5R)-2-hydroxymethyl-5-(6-(1-(4-nitrophenyl)-pyrrolidin-3(S)-ylamino)-purin-9-yl) tetrahydrofuran-3,4-diol, (2R,3R,4S,5R)-2-hydroxymethyl-5-[6-(5'-trifluoromethyl-3,4,5,6-tetrahydro-2H-[1,2']- bipyridinyl-3-yl)-purin-9-yl]tetrahydrofuran-3,4-diol, (2R,3R,4S,5R)-2-hydroxymethyl-5-[6-(phenylpyrrolidin-3(S)-ylamino)-purin-9-yl(tetrahydrofuran-3,4-diol, (2R,3R,4S,5R)-2-hydroxymethyl-5-[6-(1-pyridin-2-ylpyrrolidin-3(S)-ylamino]-purin-9-yl]tetrahydrofuran-3,4-diol, (2R,3R,4S,5R)-2-hydroxymethyl-5-[6-[1-(4-chlorophenyl)-pyrrolidin-3(S)-ylamino]-purin-9-yl]-tetrahydrofuran-3,4-diol, (2R,3R,4S,5R)-2-hydroxymethyl-5-[6-[1-(5-methylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(5-thiophen-2-ylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(5-methylmercaptopyridin-2-yl)-pyrrolidin-3(S)-ylamino]-purin-9-yl]tetrahydrofuran-3,4-diol, (2R,3R,4S,5R)-2-hydroxymethyl-5-[6-[1-(6-methoxypyrimidin-4-yl)pyrrolidin-3(S)-ylamino]-purin-9-yl]tetrahydrofuran-3,4-diol, (2R,3R,4S,5R)-2-hydroxymethyl-5-[6-[1-(6-chloropyrimidin-4-yl)pyrrolidin-3(S)-ylamino]-purin-9-yl]-tetrahydrofuran-3,4-diol, (2R,3R,4S,5R)-2-hydroxymethyl-5-[6-[1-(6-chloropyridazin-3-yl)pyrrolidin-3-ylamino]-purin-9-yl]-tetrahydrofuran-3,4-diol, (2R,3R,4S,5R)-2-methoxymethyl-5-[6-[1-(5-trifluoromethylpyridin-2-yl)-pyrrolidin-3(S)-ylamino]-purin-9-yl]tetrahydrofuran-3,4-diol, (1S,2R,3S,4R)-2,3-dihydroxy-4-[6-[1-(5-trifluoromethylpyridin-2-yl) pyrrolidin-3-ylamino]-purin-9-yl]cyclopentanecarboxylic acid ethylamide, (1S,2R,3R,5R)-3-hydroxymethyl-5-[6-[1-(4-nitrophenyl)piperidin-4-yl]-purin-9-yl]cyclopentane-1,2-diol, (1S,2R,3R,5R)-3-hydroxymethyl-5-[6-((3S)-pyrrolidin-3-ylamino)-purin-9-yl]cyclopentane-1,2-diol dihydrochloride, (1S,2R,3R,5R)-3-hydroxymethyl-5-[6-[1-(4-nitrophenyl)pyrrolidin-3-ylamino]-purin-9-yl] cyclopentane-1,2-diol, (1S,2R,3R,5R)-3-hydroxymethyl-5-[6-[1-(5-trifluoromethylpyridin-2-yl)pyrrolidin-3(R)-ylamino]-purin-9-yl]cyclopentane-1,2-diol, (1S,2R,3R,5R)-3-hydroxymethyl-5-[6-((3R)-pyrrolidin-3-ylamino)-purin-9-yl]cyclopentane-1,2-diol, (1R,2S,3R,5R)-3-hydroxymethyl-5-[6-[1-(5-trifluoromethylpyridin-2-yl) pyrrolidin-3(S)-ylamino]-purin-9-yl]cyclopentane-1,2-diol, 4(R)-1-benzyl-4-[9-(2,3-dihydroxy-4-hydroxymethylcyclopentyl)-9H-purin-6-ylamino] pyrrolidin-2-one hydrochloride, (1R,2S,3R,5S)-5-methyl-3-[6-[1-(5-trifluoromethylpyridin-2-yl)pyrrolidin-3(S)-ylamino]-purin-9-yl]cyclopentane-1,2-diol, (1R,2S,3R,5R)-5-[6-[1-(5-bromopyridin-2-yl)pyrrolidin-3(S)-ylamino]-purin-9-yl]-3-hydroxymethylcyclopentane-1,2-diol, (1R,2S,3R,5R)-5-[6-[1-(5-chloropyridin-2-yl)pyrrolidin-3(S)-ylamino]-purin-9-yl]-3-hydroxymethylcyclopentane-1,2-diol, (1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, (1R,2S,3R,5R)-3-hydroxymethyl-5-[6-[1-(pyridin-2-yl)pyrrolidin-3(S)-ylamino]-purin-9-yl]cyclopentane-1,2-diol, 4(S)-1-benzyl-4-[9-(2,3-dihydroxy-4-hydroxymethylcyclopentyl)-9H-purin-6-ylamino]pyrrolidin-2-one hydrochloride, (1R,2S,3R,5R)-3-hydroxymethyl-5-[6-[1-(quinolin-3-yl)pyrrolidin-3(S)-ylamino]-purin-9-yl]cyclopentane-1,2-diol, (1R,2S,3R,5R)-3-hydroxymethyl-5-[6-[1-S-(4-nitrophenyl)-pyrrolidin-3(S)-ylamino]-purin-9-yl]cyclopentane-1,2-diol, (1R,2S,3R,5R)-5-[6-[1-(4,5-bistrifluorpyridin-2-yl) pyrrolidin-3(S)-ylamino]-purin-9-yl]-3-hydroxymethylcyclopentane-1,2-diol, (1R,2S,3R,5R)-3-methoxymethyl-5-[6-[1-(5-trifluoromethylpyridin2-yl) pyrrolidin-3(S)-ylamino]-purin-9-yl]cyclopentane-1,2-diol, (1R,2S,3R,5R)-3-hydroxymethyl-5-[6-[1-(phenyl)-pyrrolidin-3(S)-ylamino]-purin-9-yl]cyclopentane-1,2-diol, 4-[3(S)-[9-(2,3-dihydroxy-4-hydroxymethylcyclopentyl)-

9H-purin-6-ylamino]pyrrolidin-1-yl]benzonitrile, (1R,2S,3R,5R)-3-hydroxymethyl-5-[6-[1-(isoquinolin-1-yl)pyrrolidin-3(S)ylamino]-purin-9-yl]cyclopentane-1,2-diol, (1R,2S,3R,5R)-5-[6-[1-(6-bromoquinolin-2-yl)pyrrolidin-3(S)-ylamino]-purin-9-yl]-3-hydroxymethylcyclopentane-1,2-diol, (1R,2S,3R,5R)-5-[6-[1-(4-chlorophenyl)pyrrolidin-3(S)-ylamino]-purin-9-yl]-3-hydroxymethylcyclopentane-1,2-diol, (1R,2S,3R,5R)-3-[6-[1-(3-chloro-5-trifluoromethylpyridin-2-yl)pyrrolidin-3(S)-ylamino]-purin-9-yl]-3-methoxymethylcyclopentane-1,2-diol, (1R,2S,3R,5R)-3-isopropoxymethyl-5-[6-[1-(5-trifluoromethylpyridin2-yl)pyrrolidin-3(S)-ylamino]-purin-9-yl]cyclopentane-1,2-diol, (1R,2S,3R,5R)-3-isopropoxymethyl-5-[6-[1-(4-trifluoromethylpyridin2-yl)pyrrolidin-3(S)-ylamino]-purin-9-yl]cyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-methoxymethylcyclopentane-1,2-diol, (1R,2S,3R,5R)-5-[6-[1-(6-chloropyridazin-3-yl)pyrrolidin-3(S)-ylamino]-purin-9-yl]-3-hydroxymethylcyclopentane-1,2-diol, (1R,2S,3R,5R)-3-methoxymethyl-5-[6-[1-(6-methoxypyrimidin-4-yl)pyrrolidin-3(S)-ylamino]-purin-9-yl]cyclopentane-1,2-diol, (1R,2S,3R,5R)-5-[6-[1-(6-chloropyridazin-3-yl)pyrrolidin-3(S)-ylamino]-purin-9-yl]-3-methoxymethylcyclopentane-1,2-diol, (1R,2S,3R,5R)-5-(-[6-[1-(4-trifluoromethylphenyl)-pyrrolidin-3(S)-ylamino]-purin-9-yl]-3-hydroxymethylcyclopentane-1,2-diol, (1R,2S,3R,5R)-5-[6-[1-(5-bromopyridin-2-yl)pyrrolidin-3(S)-ylamino]-purin-9-yl]-3-methoxymethylcyclopentane-1,2-diol, (1R,2S,3R,5R)-5-[6-[1-(5-chloropyridin-2-yl)pyrrolidin-3(S)-ylamino]-purin-9-yl]-3-methoxymethylcyclopentane-1,2-diol, (1R,2S,3R,5R)-3-methoxymethyl-5-[6-[1-(4-trifluoromethylphenyl)pyrrolidin-3(S)-ylamino]-purin-9-yl]cyclopentane-1,2-diol, (1R,2S,3R,5R)-5-(-[6-[1-(4-chlorophenyl)-pyrrolidin-3(S)ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-hydroxymethylcyclopentane-1,2-diol, (1R,2S,3R,5R)-3-methoxymethyl-5-[6-[1-phenylpyrrolidin-3-(S)-ylamino]-purin-9-yl]cyclopentane-1,2-diol, (1R,2S,3R,5R)-3-[6-(1-benzyl-pyrrolidin-3(S)-ylamino)purin-9-yl]5-hydroxymethylcyclopentane-1,2-diol, (1R,2S,3R,5R)-3-[6-(1-benzyl-pyrrolidin-3(S)-ylamino)purin-9-yl]5-methoxymethylcyclopentane-1,2-diol, 5'-N-[1(S)-methylpropyl]-N6-[1-(5-trifluoromethylpyridin-2-yl)pyrrolidin-3-(S)-yl]carbocyclic adenosine-5'-uronamide, and 5'-N-[1(R)-methylpropyl]-N6-[1-(5-trifluoromethylpyridin-2-yl)pyrrolidin-3-(S)-yl]carbocyclic adenosine-5'-uronamide.

A preferred class of compounds of the invention is described by Formula I wherein K is N, T is hydroxymethyl or methoxymethyl, A and B are hydroxy, X is

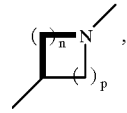

and n+p is 3 or 4, or pharmaceutically acceptable salts thereof. Representative compounds of this preferred class of compounds include (2R,3R,4S,5R)-2-hydroxymethyl-5-[6-[1-(5-chloropyridin-2-yl)-pyrrolidin-3(S)-ylamino]-purin-9-yl]-tetrahydrofuran-3,4-diol, (2R,3S,4R,5R)-2-hydroxymethyl-5-[6-[1-(5-trifluoromethylpyridin-2-yl)-pyrrolidin-3(R)-ylamino]-purin-9-yl]tetrahydrofuran-3,4-diol, (2R,3R,4S,5R)-2-hydroxymethyl-5-[6-[1-(5-trifluoromethylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(4-trifluoromethylpyridin-2-yl)-pyrrolidin-3(S)-ylamino]-purin-9-yl]tetrahydrofuran-3,4-diol, (2R,3R,4S,5R)2-hydroxymethyl-5-[6-[1-(5-bromopyridin-2-yl)-pyrrolidin-3(S)-ylamino]-purin-9-yl]-tetrahydrofuran-3,4-diol, (2R,3R,4S,5R)-2-hydroxymethyl-5-(6-(1-(4-nitrophenyl)-pyrrolidin-3(S)-ylamino)-purin-9-yl) tetrahydrofuran-3,4-diol, (2R,3R,4S,5R)-2-hydroxymethyl-5-[6-(5'-trifluoromethyl-3,4,5,6-tetrahydro-2H-[1,2']-bipyridinyl-3-yl)-purin-9-yl]tetrahydrofuran-3,4-diol, (2R,3R,4S,5R)-2-hydroxymethyl-5-[6-(phenylpyrrolidin-3(S)-ylamino)-purin-9-yl]tetrahydrofuran-3,4-diol, (2R,3R,4S,5R)-2-hydroxymethyl-5-[6-(1-pyridin-2-ylpyrrolidin-3(S)-ylamino)-purin-9-yl]tetrahydrofuran-3,4-diol, (2R,3R,4S,5R)-2-hydroxymethyl-5-[6-[1-(4-chlorophenyl)-pyrrolidin-3(S)-ylamino]-purin-9-yl]-tetrahydrofuran-3,4-diol, (2R,3R,4S,5R)-2-hydroxymethyl-5-[6-[1-(5-methylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(5-thiophen-2-ylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(5-methylmercaptopyridin-2-yl)-pyrrolidin-3(S)-ylamino]-purin-9-yl]tetrahydrofuran-3,4-diol, (2R,3R,4S,5R)-2-hydroxymethyl-5-[6-[1-(6-methoxypyrimidin-4-yl)pyrrolidin-3(S)-ylamino]-purin-9-yl]tetrahydrofuran-3,4-diol, (2R,3R,4S,5R)-2-hydroxymethyl-5-[6-[1-(6-chloropyrimidin-4-yl)pyrrolidin-3(S)-ylamino]-purin-9-yl]-tetrahydrofuran-3,4-diol, (2R,3R,4S,5R)-2-hydroxymethyl-5-[6-[1-(6-chloropyridazin-3-yl)pyrrolidin-3-ylamino]-purin-9-yl]-tetrahydrofuran-3,4-diol, (2R,3R,4S,5R)-2-methoxymethyl-5-[6-[1-(5-trifluoromethylpyridin-2-yl)-pyrrolidin-3(S)-ylamino]-purin-9-yl]tetrahydrofuran-3,4-diol, (1S,2R,3R,5R)-3-hydroxymethyl-5-[6-[1-(4-nitrophenyl)piperidin-4-yl]-purin-9-yl]cyclopentane-1,2-diol, (1S,2R,3R,5R)-3-hydroxymethyl-5-[6-((3S)-pyrrolidin-3-ylamino)-purin-9-yl]cyclopentane-1,2-diol dihydrochloride, (1S,2R,3R,5R)-3-hydroxymethyl-5-[6-[1-(4-nitrophenyl)pyrrolidin-3-ylamino]-purin-9-yl]cyclopentane-1,2-diol, (1S,2R,3R,5R)-3-hydroxymethyl-5-[6-[1-(5-trifluoromethylpyridin-2-yl)pyrrolidin-3(R)-ylamino]-purin-9-yl]cyclopentane-1,2-diol, (1S,2R,3R,5R)-3-hydroxymethyl-5-[6-((3R)-pyrrolidin-3-ylamino)-purin-9-yl]cyclopentane-1,2-diol, (1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol, (1R,2S,3R,5R)-5-[6-[1-(5-bromopyridin-2-yl)pyrrolidin-3(S)-ylamino]-purin-9-yl]-3-hydroxymethylcyclopentane-1,2-diol, (1R,2S,3R,5R)-5-[6-[1-(5-chloropyridin-2-yl)pyrrolidin-3(S)-ylamino]-purin-9-yl]-3-hydroxymethylcyclopentane-1,2-diol, (1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, (1R,2S,3R,5R)-3-hydroxymethyl-5-[6-[1-(pyridin-2-yl)pyrrolidin-3(S)-ylamino]-purin-9-yl]cyclopentane-1,2-diol, (1R,2S,3R,5R)-3-hydroxymethyl-5-[6-[1-(quinolin-3-yl)pyrrolidin-3(S)-ylamino]-purin-9-yl]cyclopentane-1,2-diol, (1R,2S,3R,5R)-3-hydroxymethyl-5-[6-[1-S-(4-nitrophenyl)-pyrrolidin-3(S)-ylamino]-purin-9-yl]cyclopentane-1,2-diol, (1R,2S,3R,5R)-5-[6-[1-(4,5- bistrifluorpyridin-2-yl)pyrrolidin-3(S)-ylamino]-purin-9-yl]-3-hydroxymethylcyclopentane-1,2-diol, (1R,2S,3R,5R)-3-methoxymethyl-5-[6-[1-(5-trifluoromethylpyridin2-yl)pyrrolidin-3(S)-ylamino]-purin-9-yl]cyclopentane-1,2-diol, (1R,2S,3R,5R)-3-hydroxymethyl-5-[6-[1-(phenyl)-pyrrolidin-3(S)-ylamino]-purin-9-yl]cyclopentane-1,2-diol, 4-[3(S)-[9-(2,3-dihydroxy-4-hydroxymethylcyclopentyl)-9H-purin-6-ylamino]pyrrolidin-1-yl]benzonitrile, (1R,2S,3R,5R)-3-hydroxymethyl-5-[6-[1-(isoquinolin-1-yl)pyrrolidin-3(S)-ylamino]-purin-9-yl]cyclopentane-1,2-diol, (1R,2S,3R,5R)-5-[6-[1-(6-bromoquinolin-2-yl)pyrrolidin-3(S)-ylamino]-purin-9-yl]-3-hydroxymethylcyclopentane-1,2-diol, (1R,2S,3R,5R)-5-[6-[1-(4-chlorophenyl)pyrrolidin-3(S)-ylamino]-purin-9-yl]-3-hydroxymethylcyclopentane-1,2-diol, (1R,2S,3R,5R)-3-[6-[1-(3-chloro-5-trifluoromethylpyridin-2-yl)pyrrolidin-3(S)-ylamino]-purin-9-yl]-3-methoxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-methoxymethylcyclopentane-1,2-diol, (1R,2S,3R,5R)-5-[6-[1-(6-chloropyridazin-3-yl)pyrrolidin-3(S)-ylamino]-purin-9-yl]-3-hydroxymethylcyclopentane-1,2-diol, (1R,2S,3R,5R)-3-methoxymethyl-5-[6-[1-(6-methoxypyrimidin-4-yl)pyrrolidin-3(S)-ylamino]-purin-9-yl]cyclopentane-1,2-diol, (1R,2S,3R,5R)-5-[6-[1-(6-chloropyridazin-3-yl)pyrrolidin-3(S)-ylamino]-purin-9-yl]-3-methoxymethylcyclopentane-1,2-diol, (1R,2S,3R,5R)-5-(-[6-[1-(4-trifluoromethylphenyl)-pyrrolidin-3(S)-ylamino]-purin-9-yl]-3-hydroxymethylcyclopentane-1,2-diol, (1R,2S,3R,5R)-5-[6-[1-(5-bromopyridin-2-yl)pyrrolidin-3(S)-ylamino]-purin-9-yl]-3-methoxymethylcyclopentane-1,2-diol, (1R,2S,3R,5R)-5-[6-[1-(5-chlorpyridin-2-yl)pyrrolidin-3(S)-ylamino]-purin-9-yl]-3-methoxymethylcyclopentane-1,2-diol, (1R,2S,3R,5R)-3-methoxymethyl-5-[6-[1-(4-trifluoromethylphenyl)pyrrolidin-3(S)-ylamino]-purin-9-yl]cyclopentane-1,2-diol, (1R,2S,3R,5R)-5-(-[6-[1-(4-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-hydroxymethylcyclopentane-1,2-diol, (1R,2S,3R,5R)-3-methoxymethyl-5-[6-[1-phenylpyrrolidin-3-(S)-ylamino]-purin-9-yl]cyclopentane-1,2-diol, (1R,2S,3R,5R)-3-[6-(1-benzyl-pyrrolidin-3(S)-ylamino)purin-9-yl]5-hydroxymethylcyclopentane-1,2-diol, and (1R,2S,3R,5R)-3-[6-(1-benzyl-pyrrolidin-3(S)-ylamino)purin-9-yl]5-methoxymethylcyclopentane-1,2-diol.

Another preferred class of compounds of the invention is described by Formula I wherein Q is CH$_2$, K is N, T is

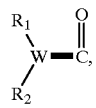

wherein R$_1$ is H and R$_2$ is lower alkyl, A and B are hydroxy, X is

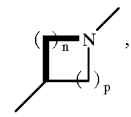

and n+p is 3 or 4, or pharmaceutically acceptable salts thereof. Representative compounds of this other preferred class of compounds include, (1S,2R,3S,4R)-2,3-dihydroxy-4-[6-[1-(5-trifluoromethylpyridin-2-yl)pyrrolidin-3-ylamino]-purin-9-yl]cyclopentanecarboxylic acid ethylamide, 5'-N-[1(S)-methylpropyl]-N6-[1-(5-trifluoromethylpyridin-2-yl)-pyrrolidin-3-(S)-yl]carbocyclic adenosine-5'-uronamide, and 5'-N-[1(R)-methylpropyl]-N6-[1-(5-trifluoromethylpyridin-2-yl)-pyrrolidin-3-(S)-yl]carbocyclic adenosine-5'-uronamide.

A more preferred class of compounds of the invention is described by Formula I wherein Q is CH$_2$, K is N, T is hydroxymethyl or methoxymethyl, A and B are hydroxy, X is

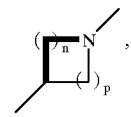

and n+p is 3 or 4, or pharmaceutically acceptable salts thereof. Representative compounds of this more preferred class of compounds include (1S,2R,3R,5R)-3-hydroxymethyl-5-[6-[1-(4-nitrophenyl)piperidin-4-yl]-purin-9-yl]cyclopentane-1,2-diol, (1S,2R,3R,5R)-3-hydroxymethyl-5-[6-((3S)-pyrrolidin-3-ylamino)-purin-9-yl]cyclopentane-1,2-diol dihydrochloride, (1S,2R,3R,5R)-3-hydroxymethyl-5-[6-[1-(4-nitrophenyl)pyrrolidin-3-ylamino]-purin-9-yl]cyclopentane-1,2-diol, (1S,2R,3R,5R)-3-hydroxymethyl-5-[6-[1-(5-trifluoromethylpyridin-2-yl)pyrrolidin-3(R)-ylamino]-purin-9-yl]cyclopentane-1,2-diol, (1S,2R,3R,5R)-3-hydroxymethyl-5-[6-((3R)-pyrrolidin-3-ylamino)-purin-9-yl]cyclopentane-1,2-diol, (1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol, (1R,2S,3R,5R)-5-[6-[1-(5-bromopyridin-2-yl)pyrrolidin-3(S)-ylamino]-purin-9-yl]-3-hydroxymethylcyclopentane-1,2-diol, (1R,2S,3R,5R)-5-[6-[1-(5-chloropyridin-2-yl)pyrrolidin-3(S)-ylamino]-purin-9-yl]-3-hydroxymethylcyclopentane-1,2-diol, (1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, (1R,2S,3R,5R)-3-hydroxymethyl-5-[6-[1-(pyridin-2-yl)pyrrolidin-3(S)-ylamino]-purin-9-yl]cyclopentane-1,2-diol, (1R,2S,3R,5R)-3-hydroxymethyl-5-[6-[1-(quinolin-3-yl)pyrrolidin-3(S)-ylamino]-purin-9-yl]cyclopentane-1,2-diol, (1R,2S,3R,5R)-3-hydroxymethyl-5-[6-[1-S-(4-nitrophenyl)-pyrrolidin-3(S)-ylamino]-purin-9-yl]cyclopentane-1,2-diol, (1R,2S,3R,5R)-5-[6-[1-(4,5-bistrifluorpyridin-2-yl)pyrrolidin-3(S)-ylamino]-purin-9-yl]-3-hydroxymethylcyclopentane-1,2-diol, (1R,2S,3R,5R)-3-methoxymethyl-5-[6-[1-(5-trifluoromethylpyridin2-yl)pyrrolidin-3(S)-ylamino]-purin-9-yl]cyclopentane-1,2-diol, (1R,2S,3R,5R)-3-hydroxymethyl-5-[6-[1-(phenyl)-pyrrolidin-3(S)-ylamino]-purin-9-yl]cyclopentane-1,2-diol, 4-[3(S)-[9-(2,3-dihydroxy-4-hydroxymethylcyclopentyl)-9H-purin-6-ylamino]pyrrolidin-1-yl]benzonitrile, (1R,2S,3R,5R)-3-hydroxymethyl-5-[6-[1-(isoquinolin-1-yl)pyrrolidin-3(S)-ylamino]-purin-9-yl]cyclopentane-1,2-diol, (1R,2S,3R,5R)-5-[6-[1-(6-bromoquinolin-2-yl)pyrrolidin-3(S)-ylamino]-purin-9-yl]-3-hydroxymethylcyclopentane-1,2-diol, (1R,2S,3R,5R)-5-[6-[1-(4-chlorophenyl)pyrrolidin-3(S)-ylamino]-purin-9-yl]-3-hydroxymethylcyclopentane-1,2-diol, (1R,2S,3R,5R)-3-[6-[1-(3-chloro-5-trifluoromethylpyridin-2-yl)pyrrolidin-3(S)-ylamino]-purin-9-yl]-3-methoxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-methoxymethylcyclopentane-1,2-diol, (1R,2S,3R,5R)-5-[6-[1-(6-chloropyridazin-3-yl)pyrrolidin-3(S)-ylamino]-purin-9-yl]-3-hydroxymethylcyclopentane-1,2-diol, (1R,2S,3R,5R)-3-methoxymethyl-5-[6-[1-(6-methoxypyrimidin-4-yl)pyrrolidin-3(S)-ylamino]-purin-9-yl]cyclopentane-1,2-diol, (1R,2S,3R,5R)-5-[6-[1-(6-chloropyridazin-3-yl)pyrrolidin-3(S)-ylamino]-purin-9-yl]-3-methoxymethylcyclopentane-1,2-diol, (1R,2S,3R,5R)-5-(-[6-[1-(4-trifluoromethylphenyl)-pyrrolidin-3(S)-ylamino]-purin-9-yl]-3-hydroxymethylcyclopentane-1,2-diol, (1R,2S,3R,5R)-5-[6-[1-(5-bromopyridin-2-yl)pyrrolidin-3(S)-ylamino]-purin-9-yl]-3-methoxymethylcyclopentane-1,2diol, (1R,2S,3R,5R)-5-[6-[1-(5-chlorpyridin-2-yl)pyrrolidin-3(S)-ylamino]-purin-9-yl]-3-methoxymethylcyclopentane-1,2-diol, (1R,2S,3R,5R)-3-methoxymethyl-5-[6-[1-(4-trifluoromethylphenyl)pyrrolidin-3(S)-ylamino]-purin-9-yl]cyclopentane-1,2-diol, (1R,2S,3R,5R)-5-(-[6-[1-(4-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-hydroxymethylcyclopentane-1,2-diol, (1R,2S,3R,5R)-3-methoxymethyl-5-[6-[1-phenylpyrrolidin-3-(S)-ylamino]-purin-9-yl]cyclopentan-1,2-diol, (1R,2S,3R,5R)-3-[6-(1-benzyl-pyrrolidin-3(S)-ylamino)purin-9-yl]5-hydroxymethylcyclopentane-1,2-diol, and (1R,2S,3R,5R)-3-[6-(1-benzyl-pyrrolidin-3(S)-ylamino)purin-9-yl]5-methoxymethylcyclopentane-1,2-diol.

Most preferred compound of the present invention include (1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol, (1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, (1R,2S,3R,5R)-3-methoxymethyl-5-[6-[1-(5-trifluoromethylpyridin-2-yl)pyrrolidin-3(S)-ylamino]-purin-9-yl]cyclopentane-1,2-diol and (1R,2S,3R,5R)-3-methoxymethyl-5-[6-[1-(4-trifluoromethylpyridin-2-yl)pyrrolidin-3(S)-ylamino]-purin-9-yl]cyclopentane-1,2-diol.

Compounds of this invention may be prepared by known methods or in accordance with the reaction sequences described below. The starting materials used in the preparation of compounds of the invention are known or commercially available, or can be prepared by known methods or by specific reaction schemes described herein.

Compounds of Formula I, wherein K is N, Q is O and T is $R_3O$—$CH_2$, may be prepared by reacting commercially-available 6-chloropurine riboside with various unsubstituted, alkyl, aralkyl, aryl, substituted aryl, heterocyclyl, or substituted heterocyclyl azacycloalkylamines or protected derivatives thereof (hereinafter, "appropriate starting amines") as exemplified below.

Compounds of Formula I, wherein K is N, Q is O and T is $R_1R_2N$—C=O are similarly prepared starting with the product of Reaction Scheme A. In this reaction, 6-chloropurine riboside, with the 2'- and 3'- hydroxyl groups of the ribose ring protected, is treated with an oxidant, for example a Jones reagent, and the product acid treated with either dicyclohexlcarbodiimide (DCC) or BOP-Cl in the presence of a selected amine, to yield the 5'-alkylcarboxamide derivative.

REACTION SCHEME A

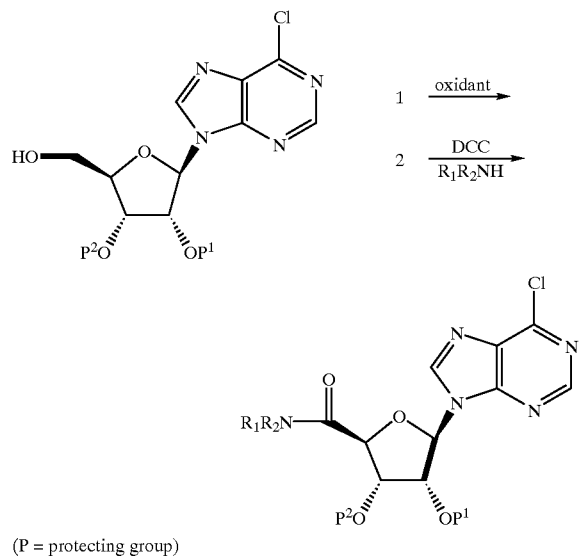

(P = protecting group)

Suitable starting materials for compounds of Formula I wherein K is N, Q is $CH_2$ and T is $R_1R_2N$—C=0, may be prepared as described by Chen et al., Tetrahedron Letters 30: 5543–46(1989). Alternatively, Reaction Scheme B may be used to prepare such starting materials. In carrying out Reaction Scheme B, the 4-ethylcarboxamide derivative of 2,3-dihydroxycyclopentylamine, prepared as described by Chen et al., is reacted with 3-amino-2,4-dichloropyrimidine. The product of this initial reaction is then heated with an aldehydylamidine acetate, for example formamidine acetate in dioxane and methoxyethanol, for a time sufficient to effect ring closure (from about 30 min to about 4 hours), thereby yielding a product which may be conveniently reacted with appropriate starting amines in the manner described below, to give the compounds of the invention. The order of reaction is not critical. For example, the intermediate formed in Reaction Scheme B could be reacted with an appropriate starting amine, followed by ring closure to yield the desired final product.

REACTION SCHEME B

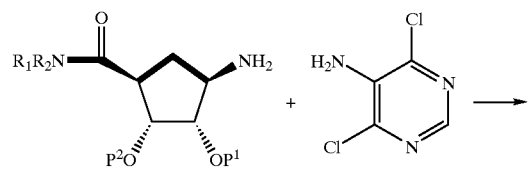

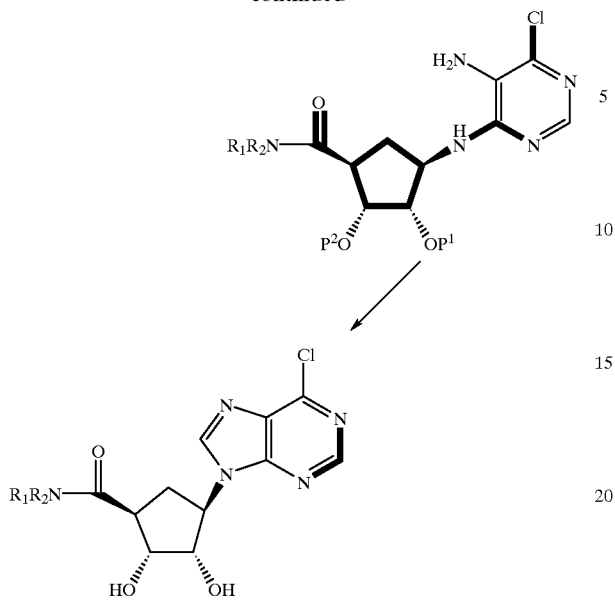

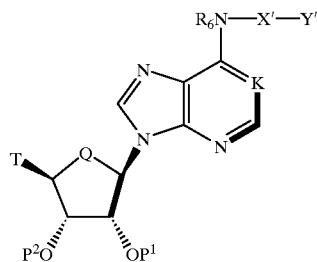

Where X' and Y' are X and Y as defined hereinabove, or protected derivatives thereof.

The N6-substituted-N'alkyl-deazaaristeromycins of the invention may be prepared as shown in Reaction Scheme D.

Various amines, useful in forming the compounds of this invention, may be prepared by methods known in the art, or by methods described herein.

Diastereomeric mixtures of compounds or intermediates useful in preparing compounds of the present may be separated into single racemic or optically active enantiomers by methods known in the art; for example, by chromatography, fractional distillation or fractional crystallization of d- or l-(tartarate, dibenzoyltartarate, mandelate or camphorsulfonate) salts.

The N6-substituted adenosines and carbocyclic adenosines of the invention may be formed by reacting 6-chloropurine riboside or the products of Reaction Schemes A or B with various appropriate starting amines, as exemplified in Reaction Scheme C.

REACTION SCHEME C

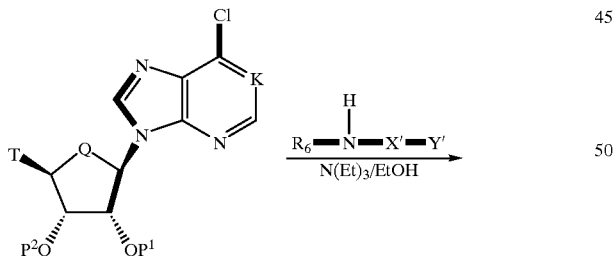

REACTION SCHEME D

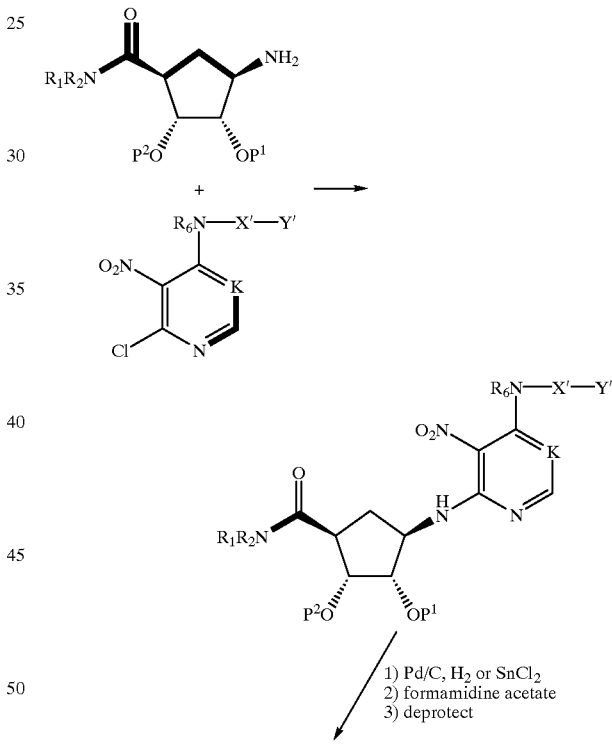

1) Pd/C, $H_2$ or $SnCl_2$
2) formamidine acetate
3) deprotect

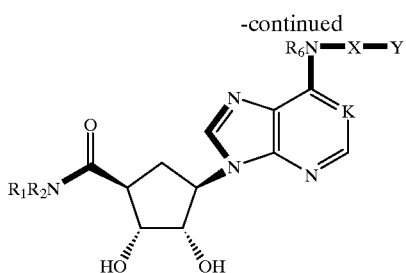
Compounds of the present invention which may act as pro-drugs include those compounds wherein the hydroxyl groups on the ribose or cyclopentane ring are substituted with groups R' and R" as defined above for Formula I. These may be prepared by known methods and are exemplified by the preparations shown in Reaction Scheme E, below.
REACTION SCHEME E
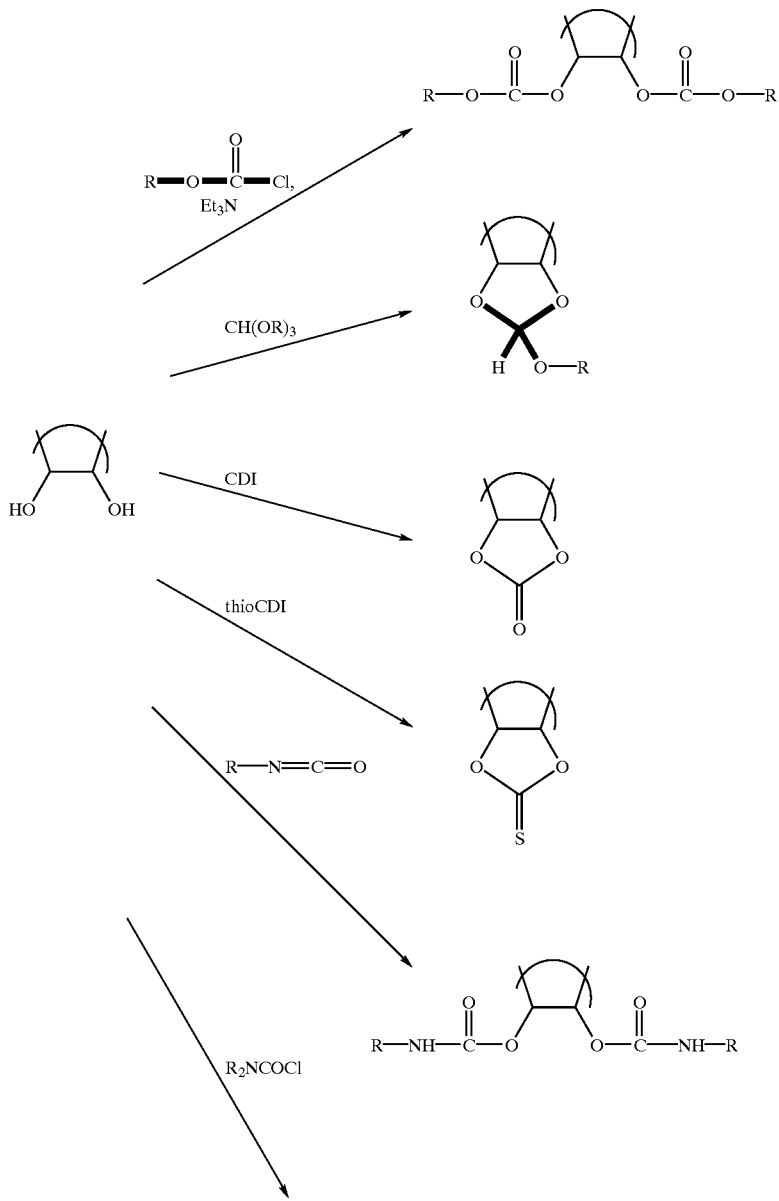

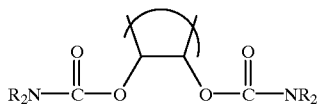

Treatment of the dihydroxy compounds with a chloroformate ester in the presence of an organic base, for example triethylamine, will give the corresponding bis-carbonate. The alkoxymethylene acetal may be prepared by treatment with the corresponding orthoester in the presence of a catalytic amount of p-toluenesulfonic acid. The carbonate is available by treatment with 1,1'-carbonyldiimidazole and the thiocarbonate by treatment with thiocarbonyldiimidizole. The alkyl and dialkylcarbamoyl derivatives may be prepared by treatment with the corresponding alkyl isocyanate or dialkyl carbamoyl chloride in the presence of an organic base respectively.

Compounds of the present invention wherein K is an N-oxides, may be prepared by oxidation of the corresponding adenosine or carbocyclic adenosine by known methods, for example by treatment with hydrogen peroxide in acetic acid.

The 2'-O-alkyl derivatives may be prepared by known methods, for example by reaction of the appropriate starting amine with 6-chloro-9-(2'-O-methyl-b-D-ribofuranosyl)-9H-purine.

Functional groups of starting compounds and intermediates that are used to prepare the compounds of the invention may be protected by common protecting groups known in the art. Conventional protecting groups for amino and hydroxyl functional groups are described, for example, in T. W. Greene, "Protective Groups in Organic Synthesis", Wiley, New York (1984).

Hydroxyl groups may be protected as esters, such as acyl derivatives, or in the form of ethers. Hydroxyl groups on adjacent carbon atoms may advantageously be protected in the form of ketals or acetals. In practice, the adjacent 2' and 3' hydroxyl groups of the starting compounds in Reaction Schemes A and B are conveniently protected by forming the 2',3' isopropylidene derivatives. The free hydroxyls may be restored by acid hydrolysis, for example, or other solvolysis or hydrogenolysis reactions commonly used in organic chemistry.

Following synthesis, compounds of the invention are typically purified by medium pressure liquid chromatography (MPLC), on a chromatotron, radially accelerated thin layer chromatography, flash chromatography or column chromatography through a silica gel or Florisil matrix, followed by crystallization. For compounds of Formula I wherein K is N, Q is O and T is $R_3O—CH_2$, typical solvent systems include chloroform:methanol, ethyl acetate:hexane, and methylene chloride:methanol. Eluates may be crystallized from methanol, ethanol, ethyl acetate, hexane or chloroform, etc.

For compounds of Formula I, wherein K is N, Q is O, and T is $R_1R_2N—C=O$, typical solvent systems include chloroform:methanol. For example, eluates may be crystallized from 50–100% ethanol (aqueous).

For compounds of Formula I, wherein Q is $CH_2$, K is N or CH, and T is $R_1R_2N—C=O$, typical solvent systems include methylene chloride:methanol. For example, eluates may be crystallized from ethyl acetate with or without methanol, ethanol or hexane.

Compounds requiring neutralization may be neutralized with a mild base such as sodium bicarbonate, followed by washing with methylene chloride and brine. Products which are purified as oils are sometimes triturated with hexane/ethanol prior to final crystallization.

The method of the present invention is further illustrated and explained by the following Examples.

EXAMPLE 1

Preparation of 5'-N-Ethyl-2',3'-isopropylidene- $N^6$-chloroadenosine-5'-uronamide Step 1: $N^6$-Chloro-2',3'-isopropylideneadenosine 6-Chloropurine riboside (31.5 g), triethylorthoformate (73 mL) and TsOH (19.8 g) are stirred in 600 mL acetone for 2 hours at RT. The reaction mixture is concentrated in vacuo, combined with ethyl acetate and washed with saturated $NaHCO_3$ solution, and brine, dried ($Na_2SO_4$) and concentrated to yield $N^6$-Chloro-2',3'-isopropylideneadenosine as a white solid.

Step 2: $N^6$-Chloro-2',3'-Isopropylideneadenosine-5'-carboxylic acid $N^6$-Chloro-2',3'-isopropylideneadenosine (4.5 g, 13.8 mmol) and 4-hydroxy-2,2,6,6-tetramethylpiperidinyloxy benzoate (4-hydroxy-TEMPO benzoate) (0.0381 g, 0.14 mmol) are combined in acetonitrile, 5% $NaHCO_3$ (87%) is added to the reaction mixture and sodium bromite hydrate (10.41 g, 55.1 mmol) is added portionwise at 0–5° C. The reaction mixture is then allowed to warm to room temperature, and the solution was stirred vigorously for about 3 hours. 10% tartaric acid solution is added and the aqueous layer is separated and extracted with ethyl acetate (3×). The combined organic layers are washed with 5% sodium bicarbonate solution (3×). The basic layers are combined and reacidified to pH 3 with concentrated hydrochloric acid. The aqueous layers are extracted with ethyl acetate (3×). The combined organic layers are then washed with brine and dried over magnesium sulfate. The filtrate is concentrated to an amorphous white solid, co-evaporated with 3 portions of toluene and dried in vacuo to give $N^6$-chloro-2',3'-isopropylideneadenosine-5'-carboxylic acid.

Step 3: 5'-N-Ethyl-2',3'-isopropylidene-$N^6$-chloroadenosine-5'-uronamide $N^6$-chloro-2',3'-isopropylideneadenosine-5'-carboxylic acid (4.4 g, 12.9 mmol), triethylamine (1.64 mL, 11.7 mmol) isopropenyl chloroformate (1.28 mL, 11.7 mmol), and methylene chloride (50 mL) are combined under argon at −10° C. and stirred for about 2 minutes. Ethylamine (0.77 mL, 11.7 mmol) is added to the reaction mixture and stirring continued for an additional 1 minute. The reaction mixture is partitioned between methylene chloride and saturated sodium bicarbonate. The aqueous layers are washed with methylene chloride (3×). The combined organic layers are washed with brine and dried over sodium sulfate, filtered, evaporated in vacuo and the residue purified by flash chromatography on silica gel, eluting with 3% MeOH/CHCl$_3$, to give 5'-N-ethyl-2',3'-isopropylidene-$N^6$-chloroadenosine-5'-uronamide, 1H NMR (300 MHz, (CDCl3) d 8.75 (s, 1H), 8.23 (s, 1H), 6.20 (d, 1H), 5.50 (dd, 2H), 4.73 (d, 1H), 3.01 (m, 2H), 1.63 (s, 1H), 1.41 (s, 3H), 0.77 (t, 3H).

EXAMPLE 2

Preparation of (1S,2R,3S,4R)-2,3-dihydroxy-4-[6-[1-(4-trifluormethylpyridin-2-yl)pyrrolidin-3(S)-ylamino]purin-9-yl]cyclopentanecarboxylic acid isopropylamide Step (1)

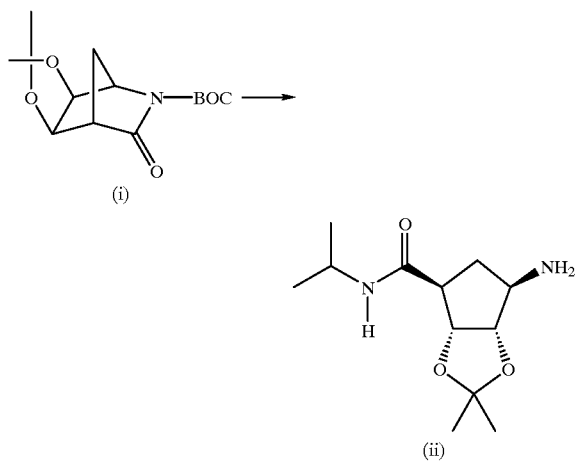

15.5 g (54.6 mmol) N-BOC-5,6-Dimethylenedioxy-2-azabicyclo[2.2.1]heptan-3-one (i) (prepared as in Step (6) of Example 3, below) is dissolved in 16 mL isopropyl amine and the mixture stirred at room temperature for about 2 hours. The mixture is evaporated in vacuo, and the residue azeotroped with chloroform to give a white solid. This solid is dissolved in 250 mL ethyl acetate, the solution cooled to 0° C., and hydrogen chloride gas is bubbled into the solution, with cooling for about 15 minutes. The solution is then stirred at room temperature for about 4 hours. The solution is evaporated in vacuo, and azeotroped with methanol, then chloroform, to give the amine product as the hydrochloride salt. The hydrochloride salt is partitioned between chloroform and sodium bicarbonate solution, and the organic layer washed with brine, dried, filtered and one equivalent of benzoic acid is added. The solvent is removed in vacuo and the residue triturated in ether to give the desired amine (ii) depicted above as the benzoate salt, m.p. 183–184° C.

Step (2) Preparation of

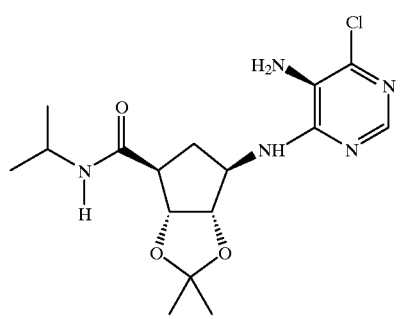

54 mmol of the product (ii) from Example 2 Step (1) above is dissolved in 110 mL n-butanol and 9.7 g 5-amino-4,6-dichloropyrimidine, then 23 mL triethylamine were added and the mixture heated at reflux for about 18 hours. The mixture is cooled, diluted with chloroform and saturated ammonium chloride solution. The aqueous layer is extracted three times chloroform, then twice with 10% isopropyl alcohol/chloroform. The organic layers are combined, dried over sodium sulfate, filtered, concentrated to an oil (iii) which is used, without further treatment for the next step.

Step (3) Preparation of

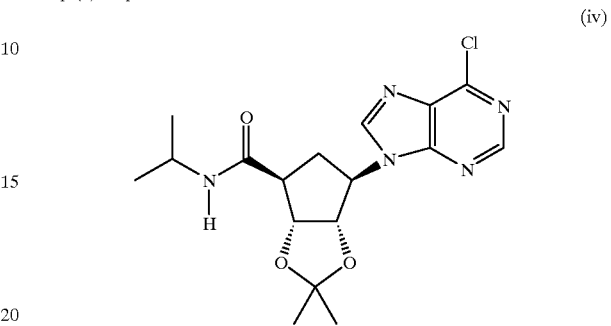

The product (iii) from Example 2 Step (2) above is taken up in 150 mL n-butyl acetate and 11.2 g formamidine acetate is added. The mixture is heated at reflux under argon for about 9 hours, adding three 5.56 g portions of formamidine acetate at two, four, and six hours. The mixture is cooled, diluted with ethyl acetate, washed with brine, water, brine, dried over sodium sulfate, filtered, concentrated in vacuo, and the residue purified by flash chromatography, eluting with 40–80% ethyl acetate in hexane, to give the desired chloropurine product (iv) depicted above.

Step (4) Preparation of

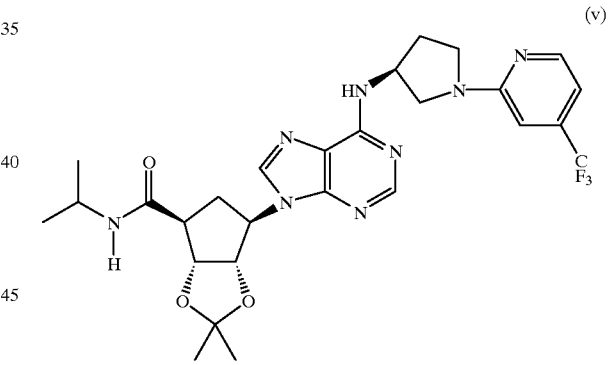

400 mg (1.05 mmol) of the product (iv) from Example 2 Step (3) above, 0.22 mL (1.57 mmol) triethylamine, and 270 mg (1.16 mmol) 2-[(3S)-3-aminopyrrolidin-1-yl]-4-trifluoromethylpyridine (prepared as in Example 3, Steps 1 to 5, below) were dissolved together in 3 mL ethanol, and the solution heated at reflux, under argon, for about 20 hours. The mixture is evaporated in vacuo and the residue partitioned between chloroform and saturated sodium bicarbonate solution. The aqueous layer is extracted with 4 portions of chloroform and the combined organic dried over sodium sulfate, filtered, evaporated in vacuo. The residue is purified by flash chromatography, applying the sample in methylene chloride/ethyl acetate (1:1), and eluting with 0 to 3% methanol in ethyl acetate, to give the above-depicted product (v).

Step (5) The product from Example 2 Step (4) above is dissolved in 2 mL methanol/tetrahydrofuran (1:1), and 3.3 mL 1.5N aqueous hydrochloric acid is added, and the solution stirred at room temperature for about 20 hours. The mixture is evaporated in vacuo. This resulting residue is taken up in 10 mL 15% isopropyl alcohol/chloroform, 1 mL 1N sodium hydroxide solution, and 9 mL saturated sodium bicarbonate solution. The layers are separated and the aqueous extracted with 4×5 mL portions of 15% isopropyl alcohol/chloroform. The combined organic layer is dried over sodium sulfate, filtered, evaporated in vacuo to give (1S,2R,3S,4R)-2,3-dihydroxy-4-[6-[1-(4-trifluormethylpyridin-2-yl)pyrrolidin-3(S)-ylamino]purin-9-yl]cyclopentanecarboxylic acid isopropylamide, m.p. 227–228° C.

EXAMPLE 3

Preparation of (1R,2S,3R,5R)-3-methoxymethyl-5-[6-[1-(5-trifluoromethylpyridin2-yl)pyrrolidin-3(S)-ylamino]-purin-9-yl]cyclopentane-1,2-diol Step (1) 20 g (232 mmol) of (3S)-(-3aminopyrrolidine and 26 mL (255 mmol, 1.1 eq) benzaldehyde are combined in 250 mL toluene and refluxed, removing water with a Dean-Stark trap, for about 4.5 hours. The mixture is cooled to 0° C. and 55.7 g (255.2 mmol, 1.1 eq) di-tert-butyl dicarbonate added, then stirred at room temperature. The mixture is concentrated in vacuo, stirred with $KHSO_4$ solution, extracted 3 times with ether. The aqueous layer is made alkaline and extracted with $CH_2Cl_2$. The organic layer is washed with brine and dried over $MgSO_4$, filtered, and evaporated in vacuo to give N1-BOC-(3S)-(-)-3 aminopyrrolidine.

Step (2) 34.25 g (183.9 mmol) of the product from Example 3 Step (1) above is dissolved in 200 mL $CH_2Cl_2$ and 25 mL (183.9 mmol) of triethylamine is added. Under a nitrogen atmosphere, 34.7 mL (367.8 mmol, 2 eq) of acetic anhydride is added dropwise, the mixture stirred at room temperature, partioned with $NaHCO_3$ solution/$CH_2Cl_2$. The organic layer is washed with brine, dried over $MgSO_4$, filtered, evaporated in vacuo, and the product purified by flash chromatography, eluting with 2–8% methanol in methylene, to give N1-BOC-(3S)-(-)-3-acetylaminopyrrolidine.

Step (3) 39.2 g (171.7 mmol) of the product from Example 3 Step (2) above is dissolved in 400 mL $CH_2Cl_2$ and 26.46 mL (343.4 mmol 2 eq) trifluoroacetic acid (hereinafter "TFA") is dropwise at at 0° C. under a nitrogen atmosphere. The mixture is heated to reflux, adding another 26 mL, then another 10 mL of TFA, refluxed for about an additional 3 hours, then evaporated under high vacuum to remove TFA. The residue was stirred with Amberlite IRA-400 basic resin (hereinafter "basic resin"), filtered, the filtrate dissolved in methanol, filtered slowly through basic resin, and the filtrate evaporated to give (3S)-(-)-3-acetylaminopyrrolidine.

Step (4) 4 g (31.2 mmol) of the product from Example 3 Step (3) above and 5.19 (40.6 mmol) 2-chloro-5-trifluoromethylpyridine are combined in 50 mL ethanol and 13 mL (93.6 mmol, 3 eq) triethylamine are added. The mixture is refluxed for about 18 hours, concentrated in vacuo and the residue partitioned between methylene chloride and sodium bicarbonate solution. The organic layer is washed with brine, dried over magnesium sulfate, filtered, evaporated in vacuo, and the residue purified by flash chromatography, eluting with 2–5% methanol in methylene chloride, to give 2-[(3S)-3-acetylaminopyrrolidin-1-yl]-5-trifluoromethylpyridine, as a solid.

Step (5) 7.52 g (27.5 mmol) of the product from Example 3 Step (4) above is combined with 75 mL 6N aqueous hydrochloric acid and the mixture refluxed for about 18 hours. The mixture is cooled to room temperature, neutralized with solid sodium bicarbonate, partitioned between dilute sodium hydroxide solution and methylene chloride. The organic layer is washed with brine, dried over magnesium sulfate, filtered, evaporated in vacuo to give 2-[(3S)-3-aminopyrrolidin-1-yl]-5-trifluoromethylpyridine.

Step (6)

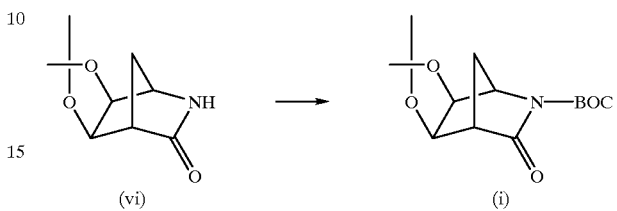

(vi)　　　　　　　(i)

22.5g (0.123 mol) (-)-5,6-Dimethylenedioxy-2-azabicyclo[2.2.1]heptan-3-one (vi), 1.5 g 4-dimethylaminopyridine (hereinafter "DMAP"), 12.4 g triethylamine, and 37.5 g di-tert-butyl dicarbonate are combined in methylene chloride and stirred at room temperature for about 18 hours. The mixture is washed with 1N hydrochloric acid, 5% sodium bicarbonate solution, brine, dried over sodium sulfate, filtered, concentrated in vacuo and the residue recrystallized from isopropyl alcohol to give N-BOC-5,6-Dimethylenedioxy-2-azabicyclo[2.2.1]heptan-3-one (i).

Step (7)

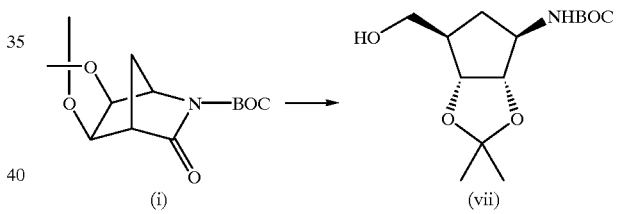

(i)　　　　　　　(vii)

35.6 g (0.125 mol) of the product (i) from Example 3 Step (6) above is combined with 400 mL methanol. With rapid stirring and cooling, under argon purge, a total of 23.8 g (0.63 mol) sodium borohydride is added in three equal portions over a period of about 2 hours. The mixture is concentrated in vacuo and partitioned between 200 mL water and 300 mL ethyl acetate. The aqueous layer is extracted twice more with ethyl acetate and the combined organic solution washed with water, brine, dried over sodium sulfate, filtered, concentrated in vacuo to give N-BOC-1-amino-2,3-dimethylenedioxy-4-hydroxymethylcyclopentane (vii).

Step (8)

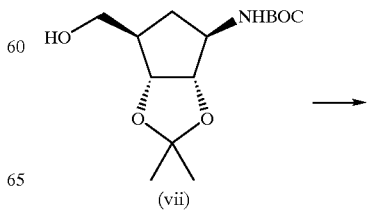

(vii)

-continued

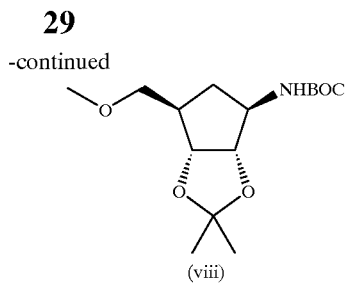

(viii)

50 g of the product (vii) from Example 3 Step (7) above is placed in 150 mL benzene. 8.8 ml methyl iodide and 33 g silver oxide are added and the mixture refluxed for about 18 hours. Another 25 g of silver oxide and another 50 mL of methyl iodide are added portionwise over about 6 hours and the mixture refluxed for about 18 hours. The mixture is filtered through Celite and the filter cake washed with ethyl acetate. The combined filtrate is concentrated in vacuo and the residue crystallized from hexane to give the desired methoxymethyl compound (viii) depicted above.

Step (9)

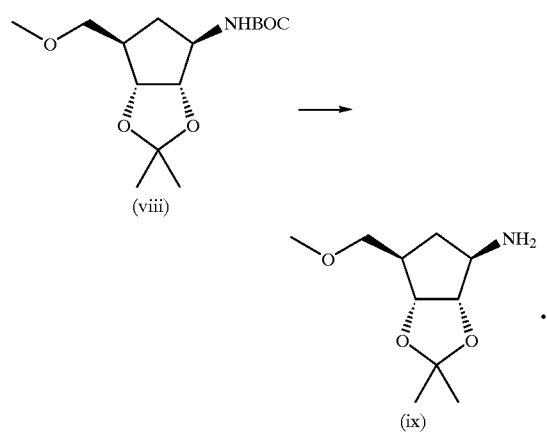

Under argon, 31.6 g of the product (viii) from Example 3 Step (8) above is dissolved in 250 mL warm anhydrous ethyl acetate. The solution is cooled in an ice bath and hydrogen chloride gas is bubbled through the solution for about 6 minutes. The mixture is allowed to warm to room temperature and stirred for about 3 hours, then concentrated in vacuo to give the desired amine hydrochloride (ix) depicted above.

Step (10)

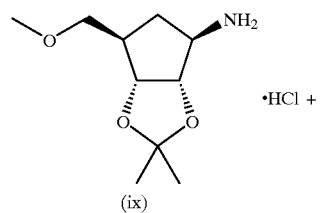

-continued

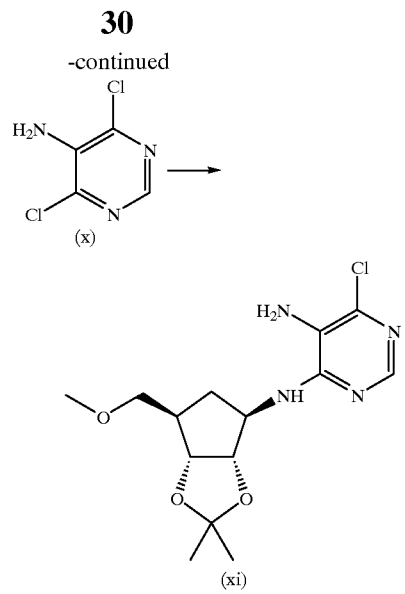

24.2 g of the product from (ix) Example 3 Step (9) above and 42.8 g sodium bicarbonate are combined in 100 mL n-butanol, under argon, and 20.1 g 5-amino-4,6-dichloro pyrimidine is added. The mixture is heated at reflux for about 20 hours, then concentrated in vacuo. The residue is partioned between ethyl acetate and water and the ethyl acetate layer washed with brine, dried over magnesium sulfate, filtered, concentrated in vacuo. The residue in 30% ethyl acetatate in hexane, passed through a large flash silica gel wash column, and the column is washed with 50% ethyl acetate/hexane and the combined filtrates concentrated in vacuo to give the desired pyrimidinylaminocyclopentane product (xi) depicted above.

Step (11)

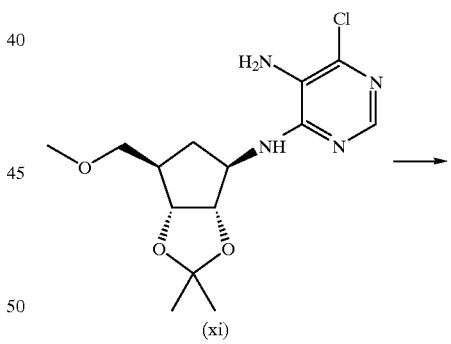

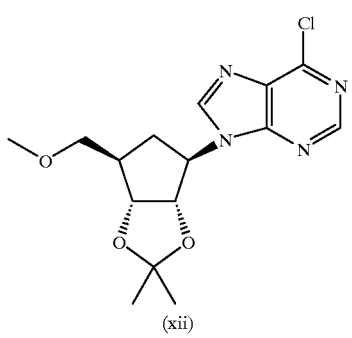

26.7 g of the product (xi) from Example 3 Step (10) above is combined with 125 mL n-butyl acetate under argon. 33.5 g formamidine acetate added and mixture heated at reflux for about 3 hours, until thin layer chromatography shows reaction is complete. The mixture is cooled, partitioned between ethyl acetate and brine and the ethyl acetate layer dried over magnesium sulfate, filtered, concentrated in vacuo. The residue was purified by flash chromatography, eluting with 30–50% ethyl acetate in hexane, to give the chloropurine product (xii) depcited above.

Step (12) Preparation of (xiii)

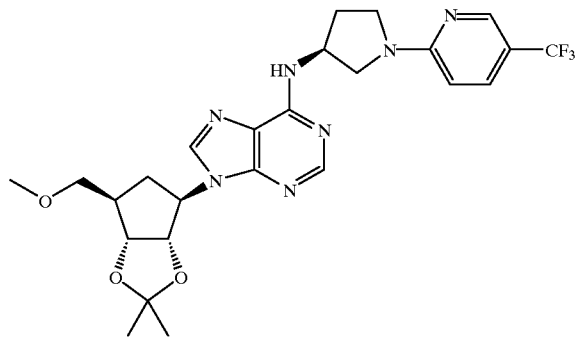

7.75 g (22.9 mmol) of the product (xii) from Example 3 Step (11) above and 6.35 g (27.4 mmol) 2-[(3S)-3-aminopyrrolidin-1-yl]-5-trifluoromethylpyridine are combined in 20 mL ethanol and 6.33 mL triethylamine added. The mixture is heated in a sealed vessel at 105° C. for about 4 hours. The mixture is cooled, evaporated in vacuo, partitioned between methylene chloride and sodium bicarbonate solution. The organic layer is dried over magnesium sulfate, filtered, concentrated in vacuo, and the residue purified by flash chromatography, eluting with 4% methanol in methylene chloride, to give the product (xiii) indicated.

Step (13) 10.81 g (20.3 mmol) of the product (xiii) from Example 3 Step (12) above is combined with 90 mL trifluoroacetate and 10 mL water, and the mixture stired at room temperature for about 30 minutes. The TFA is evaporated off at high vacuum and the residue partitioned between methylene chloride and sodium bicarbonate solution. The methylene chloride solution is washed with sodium bicarbonate solution, brine, isopropyl alcohol is added and the solution dried over magnesium sulfate, filtered, concentrated in vacuo, and the residue flash chromatographed, eluting with 5–10% methanol in methylene chloride. The appropriate fractions are collected, concentrated, and the residue crystallized from acetonitrile to give (1R,2S,3R,5R)-3-methoxymethyl-5-[6-[1-(5-trifluoromethylpyridin2-yl)pyrrolidin-3(S)-ylamino]-purin-9-yl]cyclopentane-1,2-diol, m.p. 166–168° C.

EXAMPLE 4

Preparation of (2R,3S,4R,5R)-2-hydroxymethyl-5-[6-[1-(5-trifluoromethylpyridin-2-yl)-pyrrolidin-3(R)-ylamino]-purin-9-yl]tetrahydrofuran-3,4-diol 267 mg 2-[(3R)-3-aminopyrrolidin-1-yl]-5-trifluoromethylpyridine, 331 mg 6-chloropurineriboside, 233 mg triethylamine, and 0.5 mL ethanol are combined and heated in a sealed vessel at 100° C. for about 5 hours. The mixture is cooled, partioned between methylene chloride (with some isopropyl alcohol added) and sodium bicarbonate. The organic layer is washed with brine, dried over magnesium sulfate, evaporated, and the residue purified by flash chromatography, eluting with 5% methanol in methylene chloride, to give (2R,3S,4R,5R)-2-hydroxymethyl-5-[6-[1-(5-trifluoromethylpyridin-2-yl)-pyrrolidin-3(R)-ylamino]purin-9-yl]tetrahydrofuran-3,4-diol, as the hemihydrate, m.p. 166–170° C.

EXAMPLE 5

Preparation of (1R,2S,3R,5R)-5-(-[6-[1-(4-trifluoromethylphenyl)-pyrrolidin-3(S)-ylamino]-purin-9-yl)-3-hydroxymethylcyclopentane-1,2-diol Step (1) 1.00 g (11.6 mmol) 3(S)-(-)-3-aminopyrrolidine, 1.35 mL (9.66 mmol) 4-bromobenzotrifluoride, 2.69 g (29 mmol) sodium tert-butoxide, and 1.01 g (1.16 mmol) PdCl$_2$ (P[o-tolyl]$_3$)$_2$ (prepared as in U.S. Pat. No. 4,196,135, incorporated herein by reference) are combined in 30 mL toluene, and the mixture heated in a sealed vessel at 100° C. for about 40 hours. The mixture was cooled, filtered, evaporated in vacuo and the residue purified by flash chromatography, eluting with 10:1 to 7:1 methylene chloride/ethanol, to give 1-(4-trifluoromethyl)phenyl-(3S)-pyrrolidin-3-ylamine.

Step (2)

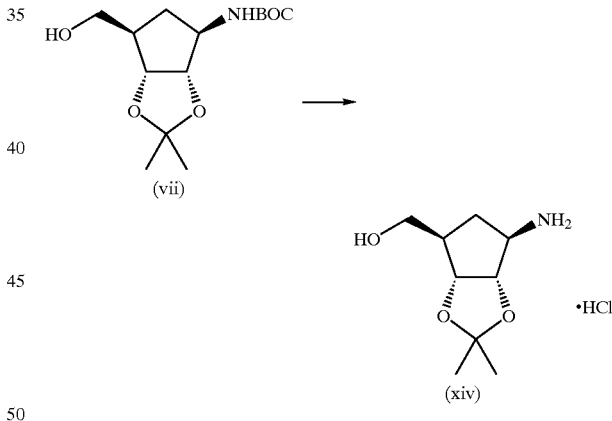

A solution of 24.7 mL (0.61 mol) methanol and 50 mL ethyl acetate is cooled to 0° C., under argon. 43.3 mL (0.61 mol) acetyl chloride is added portionwise and the solution allowed to come to room temperature over about 45 minutes. This solution is again cooled in ice and a solution of 50.0 g N-BOC-1-amino-2,3-dimethylenedioxy-4-hydroxymethyl cyclopentane (vii) in 100 mL ethyl acetate is added over a period of about 45 minutes. The solution is allowed to come to room temperature, then evaporated in vacuo to give the desired amine hydrochloride (xiv) depicted above.

Step (3) Preparation of

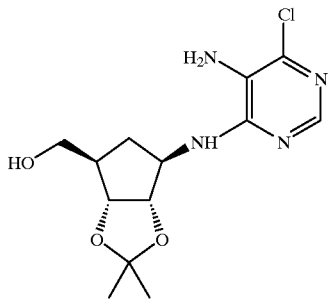
(xv)

38.9 g of the product (xiv) from Example 5 Step (2) above and 73 g sodium bicarbonate are combined in 150 mL n-butanol under argon, and the mixture stirred at room temperature for about 30 minutes. 34.2 g 5-amino-4,6-dichloropyrimidine is added and the mixture stirred at reflux for about 19 hours. The mixture is concentrated in vacuo, and the residue taken up in ethyl acetate and water. The aqueous layer is extracted with ethyl acetate and the combined organic washed with brine, filtered, concentrated in vacuo. The residue is purified by flash chromatography, eluting with a gradient of 30% to 100% ethyl acetate in hexane, to give the desired substituted chloropyrimidine (xv) depicted above.

Step (4) Preparation of

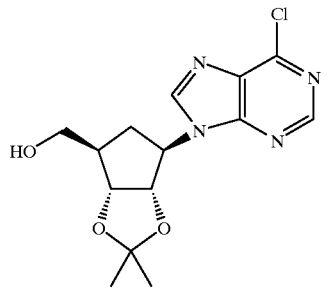
(xvi)

37.9 g of the product (xv) from Example 5 Step (3) above and 25.1 g formamidine acetate are combined in 250 mL n-butyl acetate and the mixture heated at reflux, under argon, for about 2 hours, adding an additional 12.5 g formamidine acetate after about 1 hour, and an additional 10 g after about 1.5 hours. The mixture is cooled, partitioned between ethyl acetate and brine, the brine extracted with 3 portions of ethyl acetate, and the combined organic dried over magnesium sulfate, filtered, evaporated in vacuo. The residue is purified by crystallization from ethyl acetate/hexane to give the above-depicted chloropurine (xvi). The residue from concentration of the mother liquor can be purified by flash chromatography, eluting with 80 to 100% ethyl acetate in hexane to improve recovery.

Step (5) Preparation of

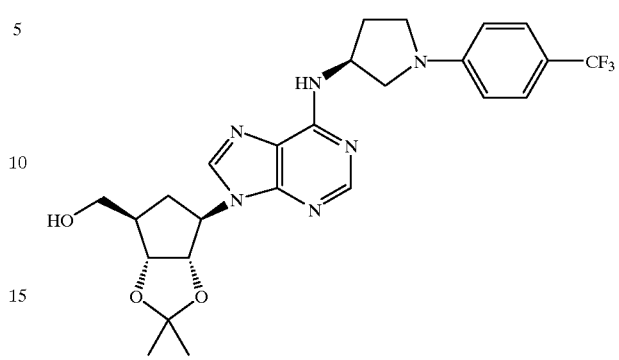
(xvii)

0.225 g (0.693 mmol) of the product (xvi) from Example 5 Step (4) above, 0.239 g (1.04 mmol) 1-(4-trifluoromethyl)phenyl-(3S)-pyrrolidin-3-ylamine, from Step (1) above, and 0.582 g (6.93 mmol) sodium bicarbonate are combined in 20 mL ethanol and heated at reflux for about 60 hours. The mixture is filtered, concentrated in vacuo, and the residue purified by flash chromatography, eluting with a gradient of methylene chloride/ethanol, 30:1 to 10:1, to give the pyrrolidinylamine (xvii) depicted above.

Step (6) 0.234 g of the product from Example 5 Step (5) above is dissolved in 10 mL trifluoroacetic acid and the solution stirred at room temperature overnight. The solution is evaporated in vacuo, and the residue purified by flash chromatography, eluting with methylene chloride/ethyl acetate (10:1) to give (1R,2S,3R,5R)-5-(-[6-[1-(4-trifluoromethylphenyl)-pyrrolidin-3(S)-ylamino]-purin-9-yl]-3-hydroxymethylcyclopentane-1,2-diol, m.p. 111–114° C.

EXAMPLE 6

Preparation of 4(S)-1-benzyl-4-[9-(2,3-dihydroxy-4-hydroxymethylcyclopentyl)-9H-purin-6-ylamino]pyrrolidin-2-one

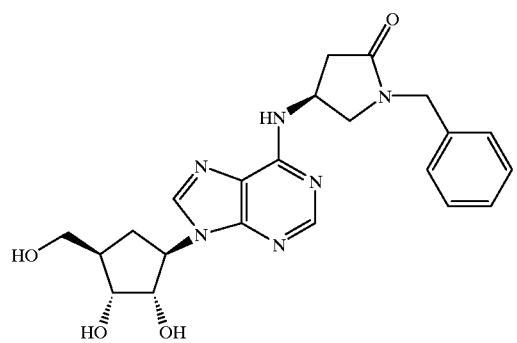
(xviii)

Step (1) Preparation of (xix)

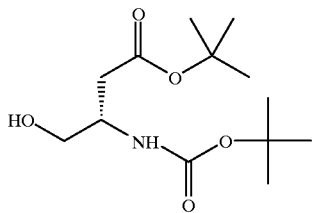

7.1 g (24.5 mmol) N-t-BOC-L- aspartic acid β-t-butyl ester is dissolved in 120 mL tetrahydrofuran. The solution is cooled to 0° C. and 2.73 g (27 mmol) triethylamine, then 2.66 g (24.5 mmol) ethyl chloroformate is added. The solution is stirred for about 30 minutes, and a solution of 3.71 g (98.2 mmol) sodium borohydride in water is added. The mixture is stirred at room temperature for about 17 hours, concentrated in vacuo and the residue diluted with ethyl acetate, and the organic layer washed with 1N hydrochloric acid, 10% sodium carbonate, brine, then dried over magnesium sulfate, filtered, concentrated in vacuo and the residue purified by flash chromatography, eluting with 30% to 50% ethyl acetate in hexane, to give 3(S)-t-butyl-3-BOC-amino-4-hydroxy-n-butanoate (xix).

Step (2) Preparation of (xx)

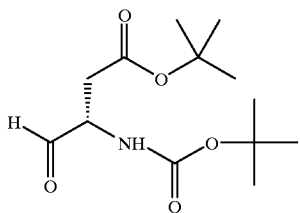

A solution of 0.73 g of dimethylsulfoxide in 9 mL of methylene chloride is cooled to −70° C. and 31 mL of a 2M solution of oxalyl chloride in methylene chloride is added dropwise. The solution is stirred for about 15 minutes and a solution of 0.85 g of 3(S)-t-butyl-3-BOC-amino-4-hydroxy-n-butanoate (xix) in 5 mL methylene chloride is added. After stirring for about 45 minutes, 1.88 g triethylamine is added. The solution is allowed to warm to room temperature, stirred for about 30 minutes, then diluted with ethyl acetate. The solution is washed with 1N hydrochloric acid, 10% sodium carbonate, brine, dried over magnesium sulfate, filtered, concentrated in vacuo, to give give 3(S)-t-butyl-3-BOC-amino-4-oxo-n-butanoate (xx).

Step (3)

(xxi)

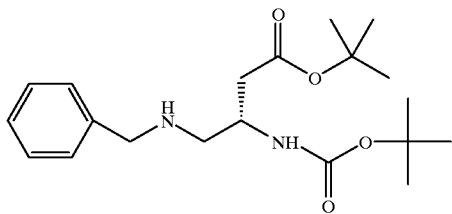

The product (xx) from Example 6 Step (2) above is dissolved in 9 mL methanol and 1.34 g benzyl amine hydrochloride, then 0.94 g triethylamine, then 200 mg 3 Å molecular seives. The solution is stirred for about 45 minutes and a solution of 0.23 g zinc chloride and 0.22 g sodium cyanoborohydride in 5 mL methanol is added. The solution is stirred for about 4 hours, 2 mL 1N sodium hydroxide, then 10 mL water are added, the mixture concentrated to about one-half volume, and extracted with ethyl acetate. The ethyl acetate solution is washed with 10% sodium carbonate solution, brine, dried over magnesium sulfate, filtered, concentrated in vacuo, and the residue purified by flash chromatography, eluting with 30% to 40% ethyl acetate in hexane, to give the benzyl amine (xxi) depicted above.

Step (4) 0.90 g of the product from Example 6 Step (3) above is dissolved in 12 mL of toluene/acetic acid (10:1), and the solution refluxed for about 1.5 hours. The mixture is concentrated in vacuo, and the residue purified by flash chromatography, eluting with 25%–35% ethyl acetate in methylene chloride, to give 1-benzyl-4(S)-BOC-amino-2-pyrrolidinone.

Step (5) 0.64 g of the product from Example 6 Step (4) above is dissolved in 20 mL ethyl acetate and the solution cooled to 0° C. Hydrogen chloride gas is bubbled into the solution for about 5 minutes, and the mixture stirred at room temperature for about 18 hours. Ether is added to the mixture and the solid collected by filtration to give 1-benzyl-4(S)-amino-2-pyrrolidinone hydrochloride.

Step (6) 0.33 g of the protected chloropurine from Example 5, Step (4) above, 0.26 g 1-benzyl-4(S)-amino-2-pyrrolidinone hydrochloride, and 0.29 g triethylamine are combined in 10 mL ethanol and the mixture heated at reflux for about 50 hours. The mixture is concentrated in vacuo and the residue dissolved in 20 mL 1N hydrochloric acid and stirred at room temperature for about 1 hour. The mixture is concentrated in vacuo and the residue purified by preparative HPLC, eluting with a gradient of 10% acetonitrile to 60% acetonitrile in water, containing 0.1% trifluoroacetic acid. The appropriate fractions were combined, concentrated, and the residue dissolved in 20 mL 1N hydrochloric acid, the solvent evaporated in vacuo, and this repeated twice more. This residue was dissolved in methanol, the solvent evaporated in vacuo, and the residue triturated in ether to give 4(S)-1-benzyl-4-[9-(2,3-dihydroxy-4-hydroxymethylcyclopentyl)-9H-purin-6ylamino]pyrrolidin-2-one as the hydrochloride trihydrate, m.p. 100° C. (dec.)

EXAMPLE 7

Preparation of (1S,2R,3R,5R)-3-hydroxymethyl-5-[6[1-(4-nitrophenyl)pyrrolidin-3-ylamino]-purin-9-yl]cyclopentane-1,2-diol Step (1) 4-nitrophenol (1.0 g, 7.19 mmol) and triethylamine (3 mL, 21.6 mmol) were dissolved together in anhydrous methylene chloride (10 mL), and the solution cooled to −15° C. Trifluoromethanesulfonic anhydride (1.81 mL, 10.8 mmol) is added and the mixture stirred at −15° C. for about 30 minutes. The mixture is diluted with methylene chloride, washed with sodium bicarbonate solution and brine, the organic layer dried over magnesium sulfate, filtered, and concentrated in vacuo. The residue is purified by flash chromatography, eluting with methylene chloride, to give 4-nitrophenyl trifluoromethanesulfonate as a light yellow solid.

Step (2) 3(S)-amino-1-benzylpyrrolidine (3.0 g, 17.0 mmol) and triethylamine (2.50 mL, 17.9 mmol) are dissolved together in anhydrous methanol (17 mL), under nitrogen, and ethyl trifluoroacetate (2.53 mL, 21.3 mmol) is added dropwise. The solution is stirred for about 18 hours, evaporated in vacuo, and the residue taken up in methylene chloride. The solution is washed with sodium bicarbonate solution, brine, dried over magnesium sulfate, filtered, concentrated in vacuo to give 1-benzyl-3(S)-trifluoroacetylaminopyrrolidine.

Step (3)Under nitrogen, 1-benzyl-3(S)-trifluoroacetylaminopyrrolidine (4.59 g, 16.7 mmol) is dissolved in anhydrous methanol (50 mL) and di-tert-butyl dicarbonate (3.68 g, 16.7 mmol) and 10% palladium on carbon (0.90 g) are added. The mixture is then stirred under hydrogen under atmospheric pressure for about 5 hours. The mixture is filtered through Celite®, rinsing with methanol, and the filtrate evaporated in vacuo, The residue was purified by flash chromatography, eluting with 5% methanol in methylene chloride to give 1-BOC-3(S) trifluoroacetylaminopyrrolidine.

Step (4)1-BOC-3(S)-trifluoroacetylaminopyrrolidine (4 g) is dissolved in methylene chloirde (130 mL) and trifluoroacetic acid (19 mL) is added. The solution is stirred at room temperature for about 1 hour, then concentrated in vacuo. The residue is partitioned between methylene chloride and saturated sodium bicarbonate solution. The layers are separated and the aqueous extracted with ethyl acetate. The combined organic is dried over magnesium sulfate, filtered, evaporated in vacuo to give 3(S)-trifluoroacetylaminopyrrolidine.

Step (5)4-Nitrophenyl trifluoromethanesulfonate (0.423 g, 1.56 mmol) and triethylamine (0.217 mL, 1.56 mmol) are dissolved together in anhydrous acetonitrile (15 mL) and 3(S)-trifluoroacetylaminopyrrolidine (0.852 g, 4.68 mmol) is added and the mixture heated at reflux for about 18 hours. The mixture is cooled, concentrated in vacuo and the residue purified by flash chromatography, eluting with a gradient of 25% to 50% ethyl acetate in hexane to give 1-(4-nitro) phenyl-3(S)-trifluoroacetylaminopyrrolidine.

Step (6)1-(4-Nitro)phenyl-3(S)-trifluoroacetylaminopyrrolidine (0.334 g, 1.10 mmol) is combined with a saturated solution of potassium carbonate in methanol/water (2:3) (20 mL), and the mixture heated at 55° C. for about two hours, then at room temperature for about 18 hours. The mixture is concentrated in vacuo and the residue taken up in water (10 mL). The aqueous is extracted with ethyl acetate, and the organic dried over magnesium sulfate, filtered, evaporated in vacuo to give 3(S)-amino-1-(4-nitro)phenylpyrrolidine.

Step (7)Using essentially the procedures of Example 3, Steps 12 and 13, and Example 5, Steps 5 and 6, (1S,2R,3R,5R)-3-hydroxymethyl-5-[6-[1-(4-nitrophenyl)pyrrolidin-3-ylamino]-purin-9-yl]cyclopentane-1,2-diol, m.p. 119–120° C., is prepared from 3(S)-amino-1-(4-nitro) phenylpyrrolidine.

Using essentially the procedures of the Reaction Schemes and Examples as described hereinabove, the following compounds are prepared from the appropriate starting materials:

(2R,3R,4S,5R)-2-hydroxymethyl-5-[6-[1-(5-chloropyridin-2-yl)-pyrrolidin-3(S)-ylamino]-purin-9-yl]-tetrahydrofuran-3,4-diol, m.p. 154–156° C.;

(2R,3R,4S,5R)-2-hydroxymethyl-5-[6-[1-(5-trifluoromethylpyridin-2-yl)-pyrrolidin-3(S)-ylamino]-purin-9-yl]tetrahydrofuran-3,4-diol, m.p. 153–156° C.;

(2R,3R,4S,5R)-2-hydroxymethyl-5-[6-[1-(4-trifluoromethylpyridin-2-yl)-pyrrolidin-3(S)-ylamino]-purin-9-yl]tetrahydrofuran-3,4-diol, m.p. 187–190° C.;

(2R,3R,4S,5R) 2-hydroxymethyl-5-[6-[1-(5-bromopyridin-2-yl)-pyrrolidin-3(S)-ylamino]-purin-9-yl]-tetrahydrofuran-3,4-diol, m.p. 153–154° C.;

(2R,3R,4S,5R)-2-hydroxymethyl-5-(6-(1-(4-nitrophenyl)-pyrrolidin-3(S)-ylamino)-purin-9-yl) tetrahydrofuran-3,4-diol, m.p. 230–232° C.;

(2R,3R,4S,5R)-2-hydroxymethyl-5-[6-(5'-trifluoromethyl-3,4,5,6-tetrahydro-2H-[1,2']-bipyridinyl-3-yl)-purin-9-yl]tetrahydrofuran-3,4-diol, m.p. 113–116° C.;

(2R,3R,4S,5R)-2-hydroxymethyl-5-[6-(phenylpyrrolidin-3(S)-ylamino)-purin-9-yl]tetrahydrofuran-3,4-diol;

(2R,3R,4S,5R)-2-hydroxymethyl-5-[6-(1-pyridin-2-ylpyrrolidin-3(S)-ylamino]-purin-9-yl] tetrahydrofuran-3,4-diol, m.p. 193–195° C.;

(2R,3R,4S,5R)-2-hydroxymethyl-5-[6-[1-(4-chlorophenyl)-pyrrolidin-3(S)-ylamino]-purin-9-yl]-tetrahydrofuran-3,4-diol, m.p. 121–124° C.;

(2R,3R,4S,5R)-2-hydroxymethyl-5-[6-[1-(5-methylpyridin-2-yl)-pyrrolidin-3(S)-ylamino]-purin-9-yl]tetrahydrofuran-3,4-diol, m.p. 164–166° C.;

(2R,3R,4S,5R)-2-hydroxymethyl-5-[6-[1-(5-thiophen-2-ylpyridin-2-yl)-pyrrolidin-3(S)-ylamino]-purin-9-yl] tetrahydrofuran-3,4-diol, 190–192° C.;

(2R,3R,4S,5R)-2-hydroxymethyl-5-[6-[1-(5-methylmercaptopyridin-2-yl)-pyrrolidin-3(S)-ylamino]-purin-9-yl]tetrahydrofuran-3,4-diol, m.p. 231–233° C.;

(2R,3R,4S,5R)-2-hydroxymethyl-5-[6-[1-(6-methoxypyrimidin-4-yl)pyrrolidin-3(S)-ylamino]-purin-9-yl]tetrahydrofuran-3,4-diol, m.p. 251–253° C.;

(2R,3R,4S,5R)-2-hydroxymethyl-5-[6-[1-(6-chloropyrimidin-4-yl)pyrrolidin-3(S)-ylamino]-purin-9-yl]-tetrahydrofuran-3,4-diol, 154–156° C.;

(2R,3R,4S,5R)-2-hydroxymethyl-5-[6-[1-(6-chloropyridazin-3-yl)pyrrolidin-3-ylamino]-purin-9-yl]-tetrahydrofuran-3,4-diol, m.p. 130° C. (dec.);

(2R,3R,4S,5R)-2-methoxymethyl-5-[6-[1-(5-trifluoromethylpyridin-2-yl)-pyrrolidin-3(S)-ylamino]-purin-9-yl]tetrahydrofuran-3,4-diol, m.p. 198–200° C.;

(1S,2R,3S,4R)-2,3-dihydroxy-4-[6-[1-(5-trifluormethylpyridin-2-yl)pyrrolidin-3-ylamino]-purin-9-yl]cyclopentanecarboxylic acid ethylamide, m.p. 135–138° C.;

(1S,2R,3R,5R)-3-hydroxymethyl-5-[6-[1-(4-nitrophenyl) piperidin-4-yl]-purin-9-yl]cyclopentane-1,2-diol, m.p. 126–128° C.;

(1S,2R,3R,5R)-3-hydroxymethyl-5-[6-((3S)-pyrrolidin-3-ylamino)-purin-9-yl]cyclopentane-1,2-diol dihydrochloride, m.p. 160° C. (dec);

(1S,2R,3R,5R)-3-hydroxymethyl-5-[6-[1-(5-trifluoromethylpyridin-2-yl)-pyrrolidin-3(R)-ylamino]-purin-9-yl]cyclopentane-1,2-diol, 175–177° C.;

(1S,2R,3R,5R)-3-hydroxymethyl-5-[6-((3R)-pyrrolidin-3-ylamino)-purin-9-yl]cyclopentane-1,2-diol, m.p. 166° C. (dec);

(1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol, m.p. 110–111 ° C.;

4(R)-1-benzyl-4-[9-(2,3-dihydroxy-4-hydroxymethylcyclopentyl)-9H-purin-6-ylamino] pyrrolidin-2-one hydrochloride, m.p. 110° C. (dec);

(1R,2S,3R,5S)-5-methyl-3-[6-[1-(5-trifluoromethylpyridin-2-yl)pyrrolidin-3(S)-ylamino]-purin-9-yl]cyclopentane-1,2-diol, m.p. 114–116° C.;

(1R,2S,3R,5R)-5-[6-[1-(5-bromopyridin-2-yl)pyrrolidin-3(S)-ylamino]-purin-9-yl]-3-hydroxymethylcyclopentane-1,2-diol, m.p. 169–171° C.;

(1R,2S,3R,5R)-5-[6-[1-(5-chloropyridin-2-yl)pyrrolidin-3(S)-ylamino]-purin-9-yl]-3-hydroxymethylcyclopentane-1,2-diol, m.p. 118–121 °C.;

(1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, m.p. 135–137° C.;

(1R,2S,3R,5R)-3-hydroxymethyl-5-[6-[1-(pyridin-2-yl)pyrrolidin-3(S)-ylamino]-purin-9-yl]cyclopentane-1,2-diol, m.p. 110–112° C.;

(1R,2S,3R,5R)-3-hydroxymethyl-5-[6-[1-(quinolin-3-yl)pyrrolidin-3(S)-ylamino]-purin-9-yl]cyclopentane-1,2-diol, m.p. 135–138° C.;

(1R,2S,3R,5R)-3-hydroxymethyl-5-[6-[1-S-(4-nitrophenyl)-pyrrolidin-3(S)-ylamino]-purin-9-yl] cyclopentane-1,2-diol;

(1R,2S,3R,5R)-5-[6-[1-(4,5-bistrifluorpyridin-2-yl)pyrrolidin-3(S)-ylamino]-purin-9-yl]-3-hydroxymethylcyclopentane-1,2-diol, m.p. 123–126° C.;

(1R,2S,3R,5R)-3-hydroxymethyl-5-[6-[1-(phenyl)-pyrrolidin-3(S)-ylamino]-purin-9-yl]cyclopentane-1,2-diol, m.p. 97–99° C.;

4-[3(S)-[9-(2,3-dihydroxy-4-hydroxymethylcyclopentyl)-9H-purin-6-ylamino] pyrrolidin-1-yl]benzonitrile, m.p. 140° C.;

(1R,2S,3R,5R)-3-hydroxymethyl-5-[6-[1-(isoquinolin-1-yl)pyrrolidin-3(S)-ylamino]-purin-9-yl]cyclopentane-1,2-diol, m.p. 119–122° C.;

(1R,2S,3R,5R)-5-[6-[1-(6-bromoquinolin-2-yl)pyrrolidin-3(S)-ylamino]-purin-9-yl]-3-hydroxymethylcyclopentane-1,2-diol;

(1R,2S,3R,5R)-5-[6-[1-(4-chlorophenyl)pyrrolidin-3(S)-ylamino]-purin-9-yl]-3-hydroxymethylcyclopentane-1,2-diol;

(1R,2S,3R,5R)-3-[6-[1-(3-chloro-5-trifluoromethylpyridin-2-yl)pyrrolidin-3(S)-ylamino]-purin-9-yl]-3-methoxymethylcyclopentane-1,2-diol, m.p. 140–143° C.;

(1R,2S,3R,5R)-5-[6-[1-(6-chloropyrimidin-4-yl)pyrrolidin-3(S)-ylamino]-purin-9-yl]-3-hydroxymethylcyclopentane-1,2-diol, m.p. 180–182° C.;

(1R,2S,3R,5R)-5-[6-[1-(6-chloropyrimidin-4-yl)pyrrolidin-3(S)-ylamino]-purin-9-yl]-3-hydroxymethylcyclopentane-1,2-diol, m.p. 125–127° C.;

(1R,2S,3R,5R)-5-[6-[1-(6-chloropyrimidin-4-yl)pyrrolidin-3(S)-ylamino]-purin-9-yl]-3-methoxymethylcyclopentane-1,2-diol;

(1R,2S,3R,5R)-5-[6-[1-(6-chloropyridazin-3-yl)pyrrolidin-3(S)-ylamino]-purin-9-yl]-3-hydroxymethylcyclopentane-1,2-diol;

(1R,2S,3R,5R)-3-methoxymethyl-5-[6-[1-(6-methoxypyrimidin-4-yl)pyrrolidin-3(S)-ylamino]-purin-9-yl]cyclopentane-1,2-diol, m.p. 118–120° C.;

(1R,2S,3R,5R)-3-isopropoxymethyl-5-[6-[1-(5-trifluoromethylpyridin2-yl)pyrrolidin-3(S)-ylamino]-purin-9-yl]cyclopentane-1,2-diol, m.p. 157–158° C.;

(1R,2S,3R,5R)-3--isopropoxymethyl-5-[6-[1-(4-trifluoromethylpyridin2-yl)pyrrolidin-3(S)-ylamino]-purin-9-yl]cyclopentane-1,2-diol, 160–161 ° C.;

(1R,2S,3R,5R)-5-[6-[1-(6-chloropyridazin-3-yl)pyrrolidin-3(S)-ylamino]-purin-9-yl]-3-methoxymethylcyclopentane-1,2-diol, m.p. 122–124° C.;

(1R,2S,3R,5R)-5-[6-[1-(5-bromopyridin-2-yl)pyrrolidin-3(S)-ylamino]-purin-9-yl]-3-methoxymethylcyclopentane-1,2-diol, m.p. 110–111° C.;

(1R,2S,3R,5R)-5-[6-[1-(5-chlorpyridin-2-yl)pyrrolidin-3(S)-ylamino]-purin-9-yl]-3-methoxymethylcyclopentane-1,2-diol, m.p. 110–112° C.;

(1R,2S,3R,5R)-3-methoxymethyl-5-[6[1-(4-trifluoromethylphenyl)pyrrolidin-3(S)-ylamino]-purin-9-yl]cyclopentane-1,2-diol, m.p. 128° C.;

(1R,2S,3R,5R)-5-(-[6-[1-(4-chlorophenyl)-pyrrolidin-3(S)-ylamino]-purin-9-yl]-3-methoxymethylcyclopentane-1,2-diol, m.p. 122–125° C.;

(1R,2S,3R,5R)-5-[6-[1-(3-chlorophenyl)-pyrrolidin-3(S)-ylamino]-purin-9-yl]-3-methoxymethylcyclopentane-1,2-diol, m.p. 127–130° C.;

(1R,2S,3R,5R)-5-[6-[1-(3-chlorophenyl)-pyrrolidin-3(S)-ylamino]-purin-9-yl]-3-hydroxymethylcyclopentane-1,2-diol, m.p. 131–133° C.; and (1R,2S,3R,5R)-3-methoxymethyl-5-[6-[1-phenylpyrrolidin-3-(S)-ylamino]-purin-9-yl] cyclopentane-1,2-diol, m.p. 106° C.

(1R,2S,3R,5R)-3-[6-(1-benzyl-pyrrolidin-3(S)-ylamino)purin-9-yl]5-hydroxymethylcyclopentane-1,2-diol, m.p. 100–102° C.;

(1R,2S,3R,5R)-3-[6-(1-benzyl-pyrrolidin-3(S)-ylamino)purin-9-yl]5-methoxymethylcyclopentane-1,2-diol, m.p. 95–96° C.

5'-N-[1(S)-methylpropyl]-N6-[1-(5-trifluoromethylpyridin-2-yl)-pyrrolidin-3-(S)-yl] carbocyclic adenosine-5'-uronamide, m.p. 215° C. (dec.); and 5'-N-[1(R)-methylpropyl]-N6-[1-(5-trifluoromethylpyridin-2-yl)-pyrrolidin-3-(S)-yl] carbocyclic adenosine-5'-uronamide, m.p. 206–212° C. (dec.).

Compounds of the present invention are useful as antihypertensive agents for the treatment of high blood pressure; they also increase coronary blood flow, and, accordingly, are useful in the treatment of myocardial ischemia; they also act as cardioprotective agents useful for the prevention or reduction of injury to the myocardium consequent to myocardial ischemia; and they also act as antilipolytic agents useful for the treatment of hyperlipidemia and hypercholesterolemia.

Compounds within the scope of this invention exhibit activity in standard $A_1/A_2$ receptor binding assays for the determination of adenosine receptor agonist activity in mammals. Exemplary test procedures which are useful in determining the receptor binding affinity of compounds of the present invention are described below.

A. IN VITRO ADENOSINE RECEPTOR BINDING AFFINITY DETERMINATION $A_1$ Receptor Binding Affinity was determined by competition assay based on ligand displacement of $^3$H-CHA (cyclohexyl adenosine) [Research Biochemicals Inc., Natick, Mass.] from receptor using a membrane preparation of whole rat brain, according to the procedure of R. F. Bruns et al., Mol. Pharmacol., 29:331 (1986). Non-specific binding was assessed in the presence of 1 mM theophylline.

$A_2$ receptor binding affinity was determined by a similar assay technique, based on ligand displacement of $^3$H-CGS 21680, a known $A_2$ receptor-specific adenosine agonist, from receptor, using membranes from rat brain striatum. Non-specific binding was assessed in the presence of 20 µM 2-chloroadenosine.

The assays were run in glass test tubes in duplicate at 25_C. Once the membranes were added, the tubes were vortexed and incubated at 25_C. for 60 minutes ($A_1$ assay) or 90 minutes ($A_2$ assay) on a rotary shaker. The assay tubes were vortexed halfway through the incubation and again near the end. The assays were terminated by rapid filtration through 2.4 cm GF/B filters using a Brandel Cell Harvestor. The test tubes were washed three times with cold 50 mM tris-HCl (pH 7.7 or 7.4), with filtration being completed within 15 seconds. The damp filter circles were placed in glass scintillation vials filled with 10 mL of Aquasol II (New England Nuclear). The vials were allowed to shake overnight on a rotary shaker and were placed into a liquid scintillation analyzer for two minute counts. $IC_{50}$ values for receptor binding, i.e. the concentration at which a compound of the invention displaced the radiolabeled standard, were obtained using a curve-fitting computer program (RS/1, Bolt, Beranek and Newman, Boston, Mass.).

$A_1$ Receptor Binding Affinity was determined also using a preparation of rat epididymal fat pad membranes.

Membrane Preparation: Rat epididymal fat pads are homogenized in buffer containing 0.25M Sucrose, 10 mM Tris, 2 mM EDTA, 0.1M phenylmethylsulfonylfluoride, and 1 µg/mL Leupeptin (200 mg wet tissue weight/mL buffer). This homogenate is placed into 50 mL centrifuge tubes and centrifuged at 1000 g (3000 RPM) for 1 minute, the intermediate supernatent is removed and centrifuged at 38,000 g for 15 minutes. The pellets are resuspended pellets in assay buffer (50 mM Tris and 1 mM EDTA) (300 mg original tissue weight/mL assay buffer), and 2 µl/ml of a solution of adenosine deaminase (10 mg/ml) is added to the suspension and the suspension incubated for 30 minutes at 37° C. The suspension is centrifuged at 38,000 g for 10 minutes, the pellet washed once with 20 ml assay buffer, the resuspended in assay buffer (1.2 g original wet tissue weight/mL buffer).

Assay and Counting: Tubes are prepared as follows: Totals (total counts bound) tubes, 100 µL membrane suspension (prepared as described above), 50 µL $^3$H-cyclohexyladenosine solution (prepared by diluting a solution of approximately 1 mCi/mL, with a specific activity of approximately 29.9 Ci/mmol, with assay buffer to 100 nM, hereinafter "CHA solution"), 350 µL assay buffer; Non-specific binding tubes, 100 µL membrane suspension, 50 µL CHA solution, 50 µL 100 µM 2-chloroadenosine in assay buffer, 300 µL assay buffer; Sample tubes, 100 µL membrane suspension, 50 µL CHA solution, 50 µL of a solution of the compound to be tested (which may be prepared from serial dilution in assay buffer of a DMSO solution), 300 µL assay buffer; Blank tubes, 50 µL CHA solution, 450 µL assay buffer. Each tube is vortexed for 10 seconds, incubated at 23° C. for two hours, and filtered using a Brandel Filtration Unit, using Whatman GF/B Filter Paper, washing twice with 5 mL 50 mM Tris. The filter discs are placed in 7 mL scintillation vials, which are then filled with approximately 5 mL Ready Safe Scintillation Cocktail, and counted.

B. IN VITRO VASORELAXATION DETERMINATION IN ISOLATED SWINE CORONARY ARTERIES

Swine coronary arteries were obtained from a local slaughter house, dissected carefully and cleaned of fat, blood and adhering tissue. Rings approximately 2–3 mm wide were cut and transferred to water-jacketed tissue baths (10 mL) filled with warm (37_C.), oxygenated ($O_2/CO_2$:95%/5%) Krebs-Henseleit buffer and mounted on L-shaped books between stainless steel rods and a force transducer. The composition of the Krebs buffer is as follows (mM): NaCl, 118; KCl, 4.7; $CaCl_2$, 2.5; $MgSO_4$ 1.2; $KH_2PO_4$, 1.2; $NaHCO_3$, 25.0; and glucose, 10.0. Rings were equilibrated for 90 minutes with frequent buffer changes at a resting tension of 5 g In order to assure optimal tension development, arterial rings were primed twice with 36 mM KCl and once with 10 µm. PGF2a, before being exposed to 3 µM PGF2a. When isometric tension had reached a steady state, accumulative doses of the adenosine analogues of the invention (usually 1 mM to 100 µM, in half logs) were added to the baths. Tension achieved with 3 µM PGF2a was considered equivalent to 100%; all other values were expressed as a percentage of that maximum. $IC_{50}$ values for relaxation, i.e. the concentration at which a compound of the invention caused a 50% reduction in tension, were determined using the above-mentioned linear curve fitting computer program.

C. IN VIVO MEAN ARTERIAL BLOOD PRESSURE (MAP) AND HEART RATE (HR) DETERMINATIONS IN NORMOTENSIVE ANESTHETIZED AND SPONTANEOUSLY HYPERTENSIVE RAT

1. Anesthetized Rat

Normotensive rats were anesthetized with sodium pentobarbital (50 mg/kg, i.p.) and placed on a heated surgical table. Cannulas were inserted into the femoral artery and veined to allow the measurement of arterial pressure and to facilitate the intravenous administration of test compounds. The animals was allowed to equilibrate for 10 minutes after surgery. Mean arterial pressure was continuously measured and recorded and heart rate was monitored using the arterial pressure pulse to trigger a cardiotachometer. After baseline parameters were established and recorded, increasing doses (1, 3, 10, 30, 100, 300 and 1000 µg/kg) of the compound of the invention to be tested were administered intravenously. Maximal changes in the cardiovascular parameters were observed after each dose of the adenosine analogue. Only one compound was administered per rat. The potency of the compounds to lower heart rate and mean arterial pressure were assessed by determining the dose of the agent necessary to lower the heart rate or arterial pressure by 25% ($ED_{25}$).

2. Spontaneously Hypertensive Rat (SHR)

The oral antihypertensive activity of compounds of the invention were examined in conscious spontaneously hypertensive rats. The rats were anesthetized with sodium pentabarbatol (50 mg/kg i.p.). A telemetry transducer was implanted into the rats abdomen via midline incision. The cannula of the transducer was inserted into the abdomenal aorta to allow direct measurement of arterial pressure in the conscious SHR. The transducer was secured to the abdomenal wall. After recovery from surgery (minimum of seven days), the SHR were placed on a receiver plate and the transducer/transmitter was activated. Systolic, diastolic and mean arterial pressure and heart rate were recorded for 1.5 hours in the unrestrained conscious rat to establish a stable baseline. Each rat then received a single dose of the compound of the invention to be tested, or vehicle, and changes in arterial pressure and heart rate were monitored for 20 hours and recorded.

When the blood flow to the heart is interrupted for brief periods of time (2 to 5 minutes), followed by restoration of blood flow (reperfusion), the heart becomes protected against the development of injury when the blood flow is interrupted for longer periods of time (for example, 30 minutes).

D. IN VITRO HEART RATE DETERMINATION

Rat isolated atria

Male Sprague-Dawley rats are anesthetized using Ketamine/Rompun and the hearts are excised quickly and placed into warm, oxygenated (95 $O_2$/5% $CO_2$) Krebs Henseleit buffer of the following composition [mM]: NaCl 118; KCl 4.7; $CaCl_2$ 2.5; $MgSO_4$ 1.2; $KH_2PO_4$ 1.2; $NaHCO_3$ 25.0 and glucose 10.0 (pH 7.4). The right, spontaneously beating, atria are dissected and suspended in water-jacketed tissue baths using stainless steel wires. Atria are equilibrated for 60 min at a resting tension of 2 g with buffer changes every 5 min for the first 15 min, then at 15 min intervals. Compounds of the present invention to be tested are added cumulatively to the baths and heart rate is determined using a Grasse® Model 7D polygraph.

Compounds of the invention exhibit activity in tests used to determine the ability of compounds to mimic the cardioprotective activity of myocardial preconditioning. Exemplary test procedures which are useful in determining the cardioprotective activity of compounds of the present invention are described below.

E. DETERMINATION OF CARDIOPROTECTIVE ACTIVITY IN RAT

1. General Surgical Preparation

Adult Sprague-Dawley rats are anesthetized with Inactin (100 mg/kg i.p.). The trachea is intubated and positive pressure ventilation is provided via a small animal respirator. Catheters are placed in the femoral vein and artery for administration of compounds of the present invention to be tested, and measurement of blood pressure, respectively. An incision is made on the left side of the thorax over the pectoral muscles, and the muscles are retracted to expose the fourth intercostal space. The chest cavity is opened and the heart is exposed. A length of 4-0 proline suture is placed through the ventricular wall near the left main coronary artery and is used to interrupt blood flow through the cornary artery by tightening a slip-knot. A pulsed-Doppler flow probe (a device which measures blood flow) is placed on the surface of the heart to confirm that the coronary artery has been porperly identified. A catheter is also placed in the left ventricle to monitor left ventricular function during the experiment.

2. Preconditioning and Test Procedures

For preconditioning the heart, the coronary artery is occluded (flow is interrupted) for a period of two minutes. The slip-knot is then released to restore flow (reperfusion) for a period of three minutes. This procedure of occlusion/reperfusion is repeated twice. Five minutes after completion of the final preconditioning event, the artery is reoccluded for 30 minutes, followed by reperfusion for three hours. When a compound of the present invention is being tested, instead of performing the occlusion/reperfusion procedure, the compound is infused for 30 minutes prior to the 30-minute occlusion period. At the conclusion of the 3-hour reperfusion period the artery is reoccluded and 1 mL of Patent Blue dye is administered into the left ventricular catheter and the heart is stopped by i.v. administration of potassium chloride. This procedure allows the dye to perfuse the normal areas of the heart while that portion of the heart that was made ischemic does not take up the dye (this is the area at risk, the "risk area"). The heart is quickly removed for analysis of infarct size. Infarct size is determined by slicing the heart from apex to base into four to five slices 1–2 mm thick. Slices are incubated in a solution of 1% triphenyltetrazolium for 15 minutes. This stain reacts with viable tissue and causes it to develop a brick-red color. The infarcted tissue does not react with the stain and is pale white in appearance. The tissue slices are placed in a video image analysis system and infarct size is determined by planimetry. The effect of the compound of the present invention tested on myocardial infarct size is assessed and used to quantitate the extent of cardioprotective activity. Results are given as the percentage of the risk area which is infarcted.

Compounds of the present invention exhibit activity in tests used to determine the ability of compounds to inhibit lipolysis. Exemplary test procedures which are useful in determining the antilipolytic activity of compounds of the present invention are described below.

F. DETERMINATION OF ANTILIPOLYTIC ACTIVITY IN RAT ADIPOCYTES

1. Isolation of Adipocytes from Epididymal Fat Pads

Adipose tissue is removed from anesthetized rats and rinsed twice in incubation medium (2.09 g sodium bicarbonate and 0.04 g EDTA, disodium salt, in 1 L Krebs buffer). Each rat (300–350 g) yields approximately 4 mL of adipose tissue. The adipose tissue (35 mL) is cut into small pieces with scissors and washed with incubation medium (50 mL). The mixture is poured into the barrel of a 50 mL syringe to which is attached a short piece of clamped tubing instead of a needle. The aqueous phase is allowed to drain. A second wash with incubation medium is passed through the syringe. The tissue is added to 50 mL of collagenase solution (collagenase (90 mg), bovine serum albumin (BSA) (500 mg), and 0.1M calcium chloride solution (1 mL), in incubation medium (50 mL)) in a 1 L bottle. The mixture is shaken in an environmental at 37° C. for about 60 minutes under an atmosphere of 95% oxygen/5% carbon dioxide to effect digestion of the tissue. The dispersed cells are poured through 2 layers of cheese cloth into a 100 mL plastic beaker. The undigested clumps in the cloth are rinsed once with incubation medium (20 mL). The cells in the beaker are centrifuged in 2 plastic tubes for 30 seconds at room temperature at 300 rpm. The aqueous phase is aspirated from beneath the loosely packed layer of floating fat cells and discarded. The adipocytes are gently poured into a 250 mL plastic beaker containing 100 mL of rinse solution (1 g BSA per 100 mL incubation medium). After gentle stirring the centrifugation step is repeated. Another wash with rinse solution follows. The cells are pooled and their volume is estimated with a graduated cylinder. The adipocytes are diluted in twice their volume of assay buffer (incubation medium (120 mL), BSA (1.2 g), pyruvic acid (13 mg)).

2. In Vitro Lipolysis Assay

The assay is performed in 20 mL plastic scintillation vials and the total assay volume is 4.2 mL. Assay buffer (2.5 mL), diluted adipocytes (1.5 mL), and a solution of the compound to be tested (12.3 µL) adenosine agonist (12.3 µl; varying concentration) is incubated in the environmental shaker for 15 minutes, then the reaction is started with norepinephrine solution (41.2 µL) (10 nM, in a carrier solution containing water (100 mL), BSA (4 mg), and 0.1M EDTA (20 µL))and adenosine deaminase (1 µg/mL, 41.2 µl). After sixty minutes in the shaker the reaction is terminated by putting the vials on ice. The contents of each vial is transferred into a 12×75 mm glass tube and centrifuged at 8–10° C. at 3600 rpm for 20 min. The hard lipid layer is removed by aspiration and the aqueous layer is assayed for glycerol (400 μl of sample). The positive control is done in the absence of any adenosine agonist, substituting water in place of the solution to be tested.

The antilipolytic activity of adenosine is mediated through activation of the $A_1$ receptor subtype. Selective agonists of the $A_2$ receptor subtype, such as CGS 21680, do not exhibit antilipolytic activity. Accordingly, while certain $A_1$ selective agonists may not have desirable antihypertensive activity and $A_2$ agonists may not be effective antilipolytic agents, compounds of the present invention which are mixed agonists are uniquely suited to effectively treat both risk factors discussed hereinabove, i.e., hypertension and hyperlipidemia.

The compounds of this invention can be normally administered orally or parenterally, in the treatment of patients suffering from hypertension, myocardial ischemia, or in patients in need of cardioprotective therapy or antilipolytic therapy. As used herein, the term "patients" includes humans and other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of the adenosine analogues to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for administration by intramuscular and subcutaneous injection. The aqueous solutions, including those of the salts dissolved in pure distilled water, are suitable for administration by intravenous injection, provided that their pH is properly adjusted, and that they are suitably buffered, made isotonic with sufficient saline or glucose and sterilized by heating or by microfiltration.

The dosage regimen used in carrying out the methods of this invention is that which insures maximum therapeutic response until improvement is obtained and thereafter the minimum effective level which gives relief. Thus, in general, the dosages are those that are therapeutically effective in lowering blood pressure in the treatment of hypertension, in increasing coronary blood flow in the treatment of myocardial ischemia, in producing a cardioprotective effect, i.e., amelioration of ischemic injury or myocardial infarct size consequent to myocardial ischemia, or in producing an antilipolytic effect. In general, the oral dose may be between about 0.1 and about 100 (preferably in the range of 1 to 10 mg/kg), and the i.v. dose about 0.01 to about 10 mg/kg (preferably in the range of 0.1 to 5 mg/kg), bearing in mind, of course, that in selecting the appropriate dosage in any specific case, consideration must be given to the patient's weight, general health, age and other factors which may influence response to the drug.

The compounds of the invention may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally about 1 to about 4 times per day. It is anticipated that many patients will require no more than about one to about two doses daily.

It is also anticipated that the present invention would be useful as an injectable dosage form which may be administered in an emergency to a patient suffering from acute hypertension or myocardial ischemia, or a patient in need of cardioprotection or antilipolytic therapy. Such treatment may be followed by intravenous infusion of the active compound and the amount of compound infused into such a patient should be effective to achieve and maintain the desired therapeutic response.

What is claimed is:

1. A compound of the formula:

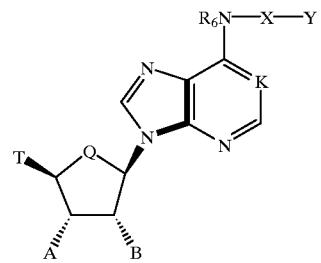

wherein:

K is N;

Q is $CH_2$ or O;

$R_6$ is hydrogen, alkyl, allyl, 2-methyl allyl, 2-butenyl, or cycloalkyl;

X is:

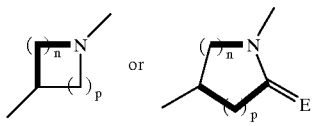

where the nitrogen of the ring of X is substituted by Y;

E is O or S;

Y is hydrogen, alkyl, aralkyl, substituted aralkyl, aryl, substituted aryl, heterocyclyl, substituted heterocyclyl, hetereocyclylalkyl, or substituted heterocyclylalkyl, said heterocyclyl having from 4 to 10 ring members comprising one or more heteroatoms selected from the group consisting of N, O and S; and n and p are independently with 0, 1, 2, or 3, provided that n+p is at least 1;

T is hydrogen, alkyl, alkyl carbonyl, alkyl thiocarbonal, halo, carboxyl

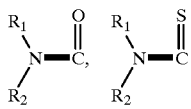

or R₃O—CH₂;

$R_1$, $R_2$ and $R_3$ are independently H, alkyl or cycloalkyl;

A is hydrogen, alkyl, hydroxyalkyl, alkoxyaokyl, or OR';

B is hydrogen, alkyl, hydroxyalkyl, alkoxyaokyl, or OR";

R' and R" are independently hydrogen, alkyl, aralkyl, carbamoyl; alkyocarbamoyl, dialkylcarbamoyl, alkylcarbonyl, alkoxycarbonyl, aralkoxycarbonyl; aryloxycarbonyl, or, when A or B are OR' and OR", respectively, R' and R" together may form

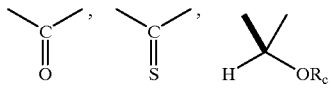

where $R_c$ is hydrogen or alkyl,

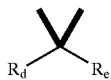

where $R_d$ and $R_e$ are independently hydrogen, alkyl, or together with the carbon atom to which they are attached may form a 1,1-cycloalkyl group;

or a pharmaceutically acceptable salt thereof, a pharamaceutically acceptable pro drug thereof, an N-oxide thereof, a hydrate thereof or a solvate thereof.

2. A compound according to claim 1 wherein K is N;

T is hydroxymethyl or methoxymethyl;

A and B are hydroxy;

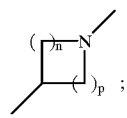

and n+p is 3 or 4;

or a pharmaceutically acceptable salt thereof, a pharamaceutically acceptable prodrug thereof, an N-oxide thereof, a hydrate thereof or a solvate thereof.

3. A compound according to claim 2 which is (2R,3R,4S, 5R)- 2-hydroxymethyl- 5-[6-[1-(5-chloropyridin-2-yl)-pyrrolidin-3(S)-ylamino]-purin-9-yl]-tetrahydrofuran-3,4-diol, (2R,3S,4R,5R)-2-hydroxymethyl-5-[6-[1-(5-trifluoromethylpyridin-2-yl)-pyrrolidin-3(R)-ylamino]-purin-9-yl]tetrahydrofuran-3,4-diol, (2R,3R,4S,5R)-2-hydroxymethyl-5-[6-[1-(5-trifluoromethylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(4-trifluoromethylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(5-bromopyridin-2-yl)-pyrrolidin-3 (S)-ylamino]-purin-9-yl]-tetrahydrofuran-3,4-diol, (2R,3R, 4S,5R)-2-hydroxymethyl-5-(6-(1-(4-nitrophenyl)-pyrrolidin-3(S)-ylamino)-purin-9-yl) tetrahydrofuran-3,4-diol, (2R,3R,4S,5R)-2-hydroxymethyl-5-[6-(5'-trifluoromethyl-3,4,5,6-tetrahydro-2H-[1,2']-bipyridinyl-3-yl)-purin-9-yl]tetrahydrofuran-3,4-diol, (2R,3R,4S,5R)-2-hydroxymethyl)-5-[6-(phenylpyrrolidin-3(S)-ylamino)-purin-9-yl]tetrahydrofuran-3,4-diol, (2R,3R,4S,5R)-2-hydroxymethyl-5-[6-(1-pyridin-2-ylpyrrolidin-3(S)-ylamino]-purin-9-yl]tetrahydrofuran-3,4-diol, (2R,3R,4S, 5R)-2-hydroxymethyl-5-[6-[1-(4-chlorophenyl)-pyrrolidin-3(S)-ylamino]-purin-9-yl]-tetrahydrofuran-3,4-diol, (2R, 3R,4S,5R)-2-hydroxymethyl-5-[6-[1-(5-methylpyridin-2-yl)-pyrrolidin-3(S)-ylamino]-purin-9-yl]tetrahydrofuran-3, 4-diol, (2R,3R,4S,5R)-2-hydroxymethyl-5-[6-[1-(5-thiophen-2-ylpyridin-2-yl)-pyrrolidin-3(S)-ylamino]-purin-9-yl]tetrahydrofuran-3,4-diol, (2R,3R,4S,5R)-2-hydroxymethyl-5-[6-[1-(5-methylmercaptopyridin-2-yl)-pyrrolidin-3(S)-ylamino]-purin-9-yl]tetrahydrofuran-3,4-diol, (2R,3R,4S,5R)-2-hydroxymethyl-5-[6-[1-(6-methoxypyrimidin-4-yl)pyrrolidin-3(S)-ylamino]-purin-9-yl]-tetrahydrofuran-3,4-diol, (2R,3R,4S,5R)-2-hydroxymethyl-5-[6-[1-(6-chloropyrimidin-4-yl)pyrrolidin-3(S)-ylamino]-purin-9-yl]-tetrahydrofuran-3,4-diol, (2R, 3R,4S,5R)-2-hydroxymethyl-5-[6-[1-(6-chloropyridazin-3-yl)pyrrolidin-3-ylamino]-purin-9-yl]-tetrahydrofuran-3,4-diol, (2R,3R,4S,5R)-2-methoxymethyl-5-[6-[1-(5-trifluoromethylpyridin-2-yl)-pyrrolidin-3(S)-ylamino]-purin-9-yl]tetrahydrofuran-3,4-diol, (1S,2R,3R,5R)-3-hydroxymethyl-5-[6-[1-(4-nitrophenyl)piperidin-4-yl]-purin-9-yl]cyclopentane-1,2-diol, (1S,2R,3R,5R)-3-hydroxymethyl-5-[6-((3S)-pyrrolidin-3-ylamino)-purin-9-yl] cyclopentane-1,2-diol dihydrochloride, (1S,2R,3R,5R)-3-hydroxymethyl-5-[6-[1-(4-nitrophenyl)pyrrolidin-3-ylamino]-purin-9-yl]cyclopentane-1,2-diol, (1S,2R,3R,5R)-3-hydroxymethyl-5-[6-[1-(5-trifluoromethylpyridin-2-yl) pyrrolidin-3(R)-ylamino]-purin-9-yl]cylcyclopentane-1,2-diol, (1S,2R,3R,5R)-3-hydroxymethyl-5-[6-((3R)-pyrrolidin-3-ylamino)-purin-9-yl]cyclopentane-1,2-diol, (1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol, (1R,2S,3R,5R)-5-[6-[1-(5-bromopyridin-2-yl)pyrrolidin-3(S)-ylamino]-purin-9-yl]-

3-hydroxymethylcyclopentane-1,2-diol, (1R,2S,3R,5R)-5-[6-[1-(5-chloropyridin-2-yl)pyrrolidin-3(S)-ylamino]-purin-9-yl]-3-hydroxymethylcyclopentane-1,2-diol, (1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, (1R,2S,3R,5R)-3-hydroxymethyl-5-[6-[1-(pyridin-2-yl)pyrrolidin-3(S)-ylamino]-purin-9-yl]cyclopentane-1,2-diol, (1R,2S,3R,5R)-3-hydroxymethyl-5-[6-[1-(quinolin-3-yl)pyrrolidin-3(S)-ylamino]-purin-9-yl]cyclopentane-1,2-diol, (1R,2S,3R,5R)-3-hydroxymethyl-5-[6-[1-S-(4-nitrophenyl)-pyrrolidin-3(S)-ylamino]-purin-9-yl]cyclopentane-1,2-diol, (1R,2S,3R,5R)-5-[6-[1-(4,5-bistrifluorpyridin-2-yl)pyrrolidin-3(S)-ylamino]-purin-9-yl]-3-hydroxymethylcyclopentane-1,2-diol, (1R,2S,3R,5R)-3-methoxymethyl-5-[6-[1-(5-trifluoromethylpyridin2-yl)pyrrolidin-3(S)-ylamino]-purin-9-yl]cyclopentane-1,2-diol, (1R,2S,3R,5R)-3-hydroxymethyl-5-[6-[1-phenyl)-pyrrolidin-3(S)-ylamino]-purin-9-yl]cyclopentane-1,2-diol, 4-[3(S)-[9-(2,3-dihydroxy-4-hydroxymethylcyclopentyl)-9H-purin-6-ylamino]pyrrolidin-1-yl]benzonitrile, (1R,2S,3R,5R)-3-hydroxymethyl-5-[6-[1-(isoquinolin-1-yl)pyrrolidin-3(S)-ylamino]-purin-9-yl]cyclopentane-1,2-diol, (1R,2S,3R,5R)-5-[6-[1-(6-bromoquinolin-2-yl)pyrrolidin-3(S)-ylamino]-purin-9-yl]-3-hydroxymethylcyclopentane-1,2-diol, (1R,2S,3R,5R)-5-[6-[1-(4-chlorophenyl)pyrrolidin-3(S)-ylamino]-purin-9-yl]-3-hydroxymethylcyclopentane-1,2-diol, (1R,2S,3R,5R)-3-[6-[1-(3-chloro-5-trifluoromethylpyridin-2-yl)pyrrolidin-3(S)-ylamino]-purin-9-yl]-3-methoxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-methoxymethylcyclopentane-1,2-diol, (1R,2S,3R,5R)-5-[6-[1-(6-chloropyridazin-3-yl)pyrrolidin-3(S)-ylamino]-purin-9-yl]-3-hydroxymethylcyclopentane-1,2-diol, (1R,2S,3R,5R)-3-methoxymethyl-5-[6-[1-(6-methoxypyrimidin-4-yl)pyrrolidin-3(S)-ylamino]-purin-9-yl]cyclopentane-1,2-diol, (1R,2S,3R,5R)-5-[6-[1-(6-chloropyridazin-3-yl)pyrrolidin-3(S)-ylamino]-purin-9-yl]-3-methoxymethylcyclopentane-1,2-diol, (1R,2S,3R,5R)-5-(-[6-[1-(4-trifluoromethylphenyl)-pyrrolidin-3(S)-ylamino]-purin-9-yl]-3-hydroxymethylcyclopentane-1,2-diol, (1R,2S,3R,5R)-5-[6-[1-(5-bromopyridin-2-yl)pyrrolidin-3(S)-ylamino]-purin-9-yl]-3-methoxymethylcyclopentane-1,2-diol, (1R,2S,3R,5R)-5-[6-[1-(5-chlorpyridin-2-yl)pyrrolidin-3(S)-ylamino]-purin-9-yl]-3-methoxymethylcyclopentane-1,2-diol, (1R,2S,3R,5R)-3-methoxymethyl-5-[6-[1-(4-trifluoromethylphenyl)pyrrolidin-3(S)-ylamino]-purin-9-yl]cyclopentane-1,2-diol, (1R,2S,3R,5R)-5-(-[6-[1-(4-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-hydroxymethylcyclopentane-1,2-diol, (1R,2S,3R,5R)-3-methoxymethyl-5-[6-[1-phenylpyrrolidin-3-(S)-ylamino)-purin-9-yl]cyclopentane-1,2-diol, (1R,2S,3R,5R)-3-[6-(1-benzyl-pyrrolidin-3(S)-ylamino]purin-9-yl]5-hydroxymethylcyclopentane-1,2-diol, or (1R,2S,3R,5R)-3-[6-(1-benzyl-pyrrolidin-3(S)-ylamino)purin-9-yl]5-methoxymethylcyclopentane-1,2-diol; or a pharmaceutically acceptable salt thereof, a pharmaceutically acceptable prodrug thereof, an N-oxide thereof, a hydrate thereof or a solvate thereof.

4. A compound according to claim 1 wherein Q is CH$_2$;

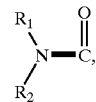

wherein R$_1$ is H and R$_2$ is lower alkyl;

K is N;

A and B are hydroxy;

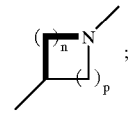

X is and n+p is 3 or 4;

or a pharmaceutically acceptable salt thereof, a pharmaceutically acceptable prodrug thereof, an N-oxide thereof, a hydrate thereof or a solvate thereof.

5. A compound according to claim 4 which is (1S,2R,3S,4R)-2,3-dihydroxy-4-[6-[1-(5-trifluormethylpyridin-2-yl)pyrrolidin-3-ylamino]-purin-9-yl]cyclopentanecarboxylic acid ethylamide, 5'-N-[1(S)-methylpropyl]-N6-[1-(5-trifluoromethylpyridin-2-yl)-pyrrolidin-3-(S)-yl]carbocyclic adenosine-5'-uronamide, or 5'-N-[1(R)-methylpropyl]-N6[1-(5-trifluoromethylpyridin-2-yl)-pyrrolidin-3-(S)-yl]carbocyclic adenosine-5'-uronamide; or a pharmaceutically acceptable salt thereof, a pharmaceutically acceptable prodrug thereof, an N-oxide thereof, a hydrate thereof or a solvate thereof.

6. A compound according to claim 1 wherein Q is CH$_2$;

K is N;

T is hydroxymethyl or methoxymethyl;

A and B are hydroxy;

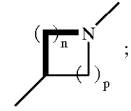

X is and n+p is 3 or 4;

or a pharmaceutically acceptable salt thereof, a pharmaceutically acceptable prodrug thereof, an N-oxide thereof, a hydrate thereof or a solvate thereof.

7. A compound according to claim 6 which is (1S,2R,3R,5R)-3-hydroxymethyl-5-[6-[1-(4-nitrophenyl)piperidin-4-yl]-purin-9-yl]cyclopentane-1,2-diol, (1S,2R,3R,5R)-3-hydroxymethyl-5-[6-((3S)-pyrrolidin-3-ylamino)-purin-9-yl]cyclopentane-1,2-diol dihydrochloride, (1S,2R,3R,5R)-3-hydroxymethyl-5-[6-[1-(4-nitrophenyl)pyrrolidin-3-ylamino]-purin-9-yl]cyclopentane-1,2-diol, (1S,2R,3R,5R)-3-hydroxymethyl-5-[6-[1-(5-trifluoromethylpyridin-2-yl)pyrrolidin-3(R)-ylamino]-purin-9-yl]cyclopentane-1,2-diol, (1S,2R,3R,5R)-3-hydroxymethyl-5-[6-((3R)-pyrrolidin-3-ylamino)-purin-9-yl]cyclopentane-1,2-diol, (1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol, (1R,2S,3R,5R)-5-[6-[1-(5-bromopyridin-2-yl)pyrrolidin-3(S)-ylamino]-purin-9-yl]-3-hydroxymethylcyclopentane-1, 2-diol, (1R,2S,3R,5R)-5-[6-[1-(5-chloropyridin-2-yl)pyrrolidin-3(S)-ylamino]-purin-9-yl]-3-hydroxymethylcyclopentane-1,2-diol, (1R,2S,3R,5R)-3-hydroxymethyl-5-[6-[1-(4-trifluoromethylpyridin-2-yl)pyrrolidin-3(S)-ylamino]-purin-9-yl]cyclopentane-1,2-diol, (1R,2S,3R,5R)-3-hydroxymethyl-5-[6-[1-(pyridin-2-yl)pyrrolidin-3(S)-ylamino]-purin-9-yl]cyclopentane-1,2-diol, (1R,2S,3R,5R)-3-hydroxymethyl-5-[6-[1-(quinolin-3-yl)pyrrolidin-3(S)-ylamino]-purin-9-yl]cyclopentane-1,2-diol, (1R,2S,3R,5R)-3-hydroxymethyl-5-[6-[1-S-(4-nitrophenyl)-pyrrolidin-3(S)-ylamino]-purin-9-yl]cyclopentane-1,2-diol, (1R,2S,3R,5R)-5-[6-[1-(4,5-bistrifluorpyridin-2-yl)pyrrolidin-3(S)-ylamino]-purin-9-yl]-1447 3-hydroxymethylcyclopentane-1,2-diol, (1R,2S,3R,5R)-3-methoxymethyl-5-[6-[1-(5-trifluoromethylpyridin2-yl)pyrrolidin-3(S)-ylamino]-purin-9-yl]cyclopentane-1,2-diol, (1R,2S,3R,5R)-3-hydroxymethyl-5-[6-[1-(phenyl)-pyrrolidin-3(S)-ylamino]-purin-9-yl]cyclopentane-1,2-diol, 4-[3(S)-[9-(2,3-dihydroxy-4-hydroxymethylcyclopentyl)-9H-purin-6-ylamino]pyrrolidin-1-yl]benzonitrile, (1R,2S,3R,5R)-3-hydroxymethyl-5-[6-[1-(isoquinolin-1-yl)pyrrolidin-3(S)-ylamino]-purin-9-yl]cyclopentane-1,2-diol, (1R,2S,3R,5R)-5-[6-[1-(6-bromoquinolin-2-yl)pyrrolidin-3(S)-ylamino]-purin-9-yl]-3-hydroxymethylcyclopentane-1,2-diol, (1R,2S,3R,5R)-5-[6-[1-(4-chlorophenyl)pyrrolidin-3(S)-ylamino]-purin-9-yl]-3-hydroxymethylcyclopentane-1,2-diol, (1R,2S,3R,5R)-3-[6-[1-(3-chloro-5-trifluoromethylpyridin-2-yl)pyrrolidin-3(S)-ylamino]-purin-9-yl]-3-methoxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-hydroxymethylcyclopentane-1,2-diol, (1R,2S,3R,5R)-5-[6-[1-(6-chloropyrimidin-4-yl)pyrrolidin-3(S)-ylamino]-purin-9-yl]-3-methoxymethylcyclopentane-1,2-diol, (1R,2S,3R,5R)-5-[6-[1-(6-chloropyridazin-3-yl)pyrrolidin-3(S)-ylamino]-purin-9-yl]-3-hydroxymethylcyclopentane-1,2-diol, (1R,2S,3R,5R)-3-methoxymethyl-5-[6-[1-(6-methoxypyrimidin-4-yl)pyrrolidin-3(S)-ylamino]-purin-9-yl]cyclopentane-1,2-diol, (1R,2S,3R,5R)-5-[6-[1-(6-chloropyridazin-3-yl)pyrrolidin-3(S)-ylamino]-purin-9-yl]-3-methoxymethylcyclopentane-1,2-diol, (1R,2S,3R,5R)-5-(-[6-[1-(4-trifluoromethylphenyl)-pyrrolidin-3(S)-ylamino]-purin-9-yl]-3-hydroxymethylcyclopentane-1,2-diol, (1R,2S,3R,5R)-5-[6-[1-(5-bromopyridin-2-yl)pyrrolidin-3(S)-ylamino]-purin-9-yl]-3-methoxymethylcyclopentane-1,2-diol, (1R,2S,3R,5R)-5-[6-[1-(5-chlorpyridin-2-yl)pyrrolidin-3(S)-ylamino]-purin-9-yl]-3-methoxymethylcyclopentane-1,2-diol, (1R,2S,3R,5R)-3-methoxymethyl-5-[6-[1-(4-trifluoromethylphenyl)pyrrolidin-3(S)-ylamino]-purin-9-yl]cyclopentane-1,2-diol, (1R,2S,3R,5R)-5-(-[6-[1-(4-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-methoxymethylcyclopentane-1,2-diol, (1R,2S,3R,5R)-5-[6-[1-(3-chlorophenyl)-pyrrolidin-3(S)-ylamino]-purin-9-yl]-3-hydroxymethylcyclopentane-1,2-diol, (1R,2S,3R,5R)-3-methoxymethyl-5-[6-[1-phenylpyrrolidin-3-(S)-ylamino]-purin-9-yl]cyclopentane-1,2-diol, (1R,2S,3R,5R)-3-[6-(1-benzyl-pyrrolidin-3(S)-ylamino)purin-9-yl]5-hydroxymethylcyclopentane-1,2-diol, or (1R,2S,3R,5R)-3-[6-(1-benzyl-pyrrolidin-3(S)-ylamino)purin-9-yl]5-methoxymethylcyclopentane-1,2-diol; or a pharmaceutically acceptable salt thereof, a pharmaceutically acceptable prodrug thereof, an N-oxide thereof, a hydrate thereof or a solvate thereof.

8. A compound according to claim 6 which is (1R,2S,3R,5R)-3-hydroxymethyl-5-[6-[1-(5-trifluoromethylpyridin-2-yl)pyrrolidin-3(S)-ylamino]-purin-9-yl]cyclopentane-1,2-diol or (1R,2S,3R,5 R)-3-hydroxymethyl-5-[6-[1-(4-trifluoromethylpyridin-2-yl)pyrrolidin-3(S)-ylamino]-purin-9-yl]cyclopentane-1,2-diol or a pharmaceutically acceptable salt thereof, a pharmaceutically acceptable prodrug thereof, an N-oxide thereof, a hydrate thereof or a solvate thereof.

9. A compound according to claim 6 which is (1R,2S,3R,5R)-3-methoxymethyl-5-[6-[1-(5-trifluoromethylpyridin-2-yl)pyrrolidin-3(S)-ylamino]-purin-9-yl]cyclopentane-1,2-diol or (1R,2S,3R,5R)-3-methoxymethyl-5-[6-[1-(4-trifluoromethylpyridin-2-yl)pyrrolidin-3(S)-ylamino]-purin-9-yl]cyclopentane-1,2-diol or a pharmaceutically acceptable salt thereof, a pharmaceutically acceptable prodrug thereof, an N-oxide thereof, a hydrate thereof or a solvate thereof.

10. The compound of claim 1, wherein K is an N-oxide.

11. A composition for treating a cardiovascular disease marked by hypertension or myocardial ischemia, for ameliorating ischemic injury or reducing myocardial infarct size consequent to myocardial ischemia, or for reducing lipid levels, triglyceride levels or cholesterol levels in a mammal, said composition comprising an effective amount of a compound according to claim 1 and a pharmaceutically acceptable carrier thereof.

12. A method for ameliorating ischemic injury in a patient in a patient suffering therefrom or reducing myocardial infarct size consequent to myocardial ischemia in a patient suffering therefrom, comprising administering to said patient an effective amount of a compound according to claim 1.

13. A method for treating a patient suffering from myocardial ischemia, comprising administering to said patient an effective antiischemic amount of a compound according to claim 1.

14. A method for treating a patient suffering from hyperlipidemia or hypercholesterolemia, comprising administering to said patient an effective antilipolytic amount of a compound according to claim 1.

15. A method for treating a patient suffering from hypertension, comprising administering to said patient an effective blood pressure lowering amount of a compound according to claim 1.

* * * * *